(12) United States Patent
Anazawa et al.

(10) Patent No.: US 7,238,325 B2
(45) Date of Patent: Jul. 3, 2007

(54) VERY SMALL CHEMICAL DEVICE AND FLOW RATE ADJUSTING METHOD THEREFOR

(75) Inventors: Takanori Anazawa, Sakura (JP); Atsushi Teramae, Yachimata (JP)

(73) Assignee: Kawamura Institute of Chemical Research, Sakura-shi (JP)

( * ) Notice: Subject to any disclaimer, the term of this patent is extended or adjusted under 35 U.S.C. 154(b) by 676 days.

(21) Appl. No.: 10/380,469

(22) PCT Filed: Mar. 1, 2001

(86) PCT No.: PCT/JP01/01563

§ 371 (c)(1),
(2), (4) Date: Mar. 20, 2003

(87) PCT Pub. No.: WO02/24320

PCT Pub. Date: Mar. 28, 2002

(65) Prior Publication Data

US 2003/0190265 A1  Oct. 9, 2003

(30) Foreign Application Priority Data

Sep. 22, 2000  (JP) .............................. 2000-288504

(51) Int. Cl.
*B01L 11/00* (2006.01)
(52) U.S. Cl. .................. 422/103; 422/99; 422/100; 422/101; 436/180; 137/67; 137/78.1; 137/803
(58) Field of Classification Search .......... 422/99–103; 436/180; 137/67, 78.1, 803
See application file for complete search history.

(56) References Cited

U.S. PATENT DOCUMENTS 5,617,632 A * 4/1997 Saaski et al. .......... 29/890.122
5,660,728 A   8/1997 Saaski et al. ................ 210/251

(Continued)

FOREIGN PATENT DOCUMENTS

EP    0450736 A1   10/1991

(Continued)

OTHER PUBLICATIONS

C. Jaroschek et al; "Harte Und Weiche Kunstoffe Beim Spritzgiessen Kombinieren" vol. 84, No. 6, pp. 705-706, 708; XP000445627 (see search report).
Supplementary European Search Report dated Nov. 16, 2004.

*Primary Examiner*—Jill Warden
*Assistant Examiner*—Jyoti Nagpaul
(74) *Attorney, Agent, or Firm*—Armstrong, Kratz, Quintos, Hanson & Brooks, LLP

(57) ABSTRACT

There is provided a micro chemical device with a valve function for which the pressure resistance is high and the channel cross-sectional area does not depend on the fluid pressure, and which furthermore enables the suppression of the adsorption of biological matter and yet is easy to produce, as well as a flow regulation method using such a device. This has a valve function, in which a member (B) is bonded to a member (A) with a groove in the surface thereof, via the surface of the member (A) in which the groove is formed, a capillary type channel of width from 1 to 1000 μm and height from 1 to 1000 μm is formed by the groove of the member (A) and the member (B) at the bonding surface between the member (A) and the member (B), a cavity section is formed partway along the channel and the width of this cavity section is from 0.5 to 100 fold the width of the capillary type channel and the ratio of maximum height/maximum width for the cavity section is no more than 1, and either one of the member (A) and the member (B) is formed from a soft material with a tensile modulus of elasticity within a range from 0.1 MPa to 700 MPa, at least within the portion which corresponds with the position of the cavity section, wherein by selectively compressing the cavity section from the external surface of the member (A) and/or the member (B), the volume of the cavity section can be reduced in a reversible manner.

25 Claims, 5 Drawing Sheets

U.S. PATENT DOCUMENTS

| | | | |
|---|---|---|---|
| 5,765,591 A | 6/1998 | Wasson et al. | 137/597 |
| 6,073,482 A | 6/2000 | Moles | 73/53.01 |

FOREIGN PATENT DOCUMENTS

| | | |
|---|---|---|
| WO | WO95/17965 | 7/1995 |
| WO | WO97/27324 | 7/1997 |
| WO | WO99/03584 | 1/1999 |
| WO | WO99/19717 | 4/1999 |
| WO | WO99/60397 | 11/1999 |

\* cited by examiner

VERY SMALL CHEMICAL DEVICE AND FLOW RATE ADJUSTING METHOD THEREFOR

TECHNICAL FIELD

The present invention relates to a micro chemical device comprising a capillary type micro channel within a member and a section which functions as a valve for controlling the flow rate of a fluid flowing through the micro channel. More specifically, the invention relates to a micro chemical device with a valve function comprising a capillary type channel and a cavity section provided partway along the channel, which are provided between laminated and bonded members, wherein by compressing the cavity section from outside the members, the channel can be opened and closed or the flow rate can be regulated, and also relates to a flow regulation method using such a device.

A micro chemical device of the present invention can be used as a micro reaction device (a micro reactor) in the fields of chemistry or biochemistry; as a microanalysis device such as an integrated DNA analysis device, a micro electrophoresis device or a micro chromatography device; as a micro device for preparing samples for analysis by mass spectrometry or liquid chromatography; or as a device for a physical chemistry process such as extraction, membrane separation or dialysis.

BACKGROUND ART

A micro chemical device formed from a silicone rubber comprising a fluid channel and a pressurizing cavity section separated from the fluid channel by a silicone rubber membrane wall was disclosed in Science Magazine (Vol. 288, page 113, 2000). Furthermore, a method for performing flow regulation of a fluid by introducing compressed air into the pressurizing cavity section, and bending the silicone rubber membrane wall so as to press onto the channel, thereby altering the cross-sectional area of the channel, was also disclosed.

However, because this micro chemical device is formed from a soft material of low rigidity, it suffers from low pressure resistance, and furthermore, the channel cross-sectional area varies with variations in the fluid pressure, and the flow rate is not proportional to the pressure. In addition, the device also has other drawbacks in that it displays a high adsorption of biochemical materials, is highly restricted in terms of potential applications, and requires a considerable length of time to form a micro structure, resulting in a marked fall in productivity.

DISCLOSURE OF INVENTION

An object of the present invention is to provide a micro chemical device with a valve function for which the pressure resistance is high and the channel cross-sectional area does not depend on the fluid pressure, and which furthermore enables the suppression of the adsorption of biological matter and yet is easy to produce, as well as a flow regulation method using such a device.

As a result of intensive investigations aimed at resolving the above problems, the inventors of the present invention discovered that by ensuring that at least one of the members in a micro chemical device with a channel formed between two members and a cavity section formed as a portion of the channel, or at least one of the members in a micro chemical device formed from three laminated members, is formed from a flexible material with a specified tensile modulus of elasticity, and then selectively compressing the cavity section from outside the member, and causing a deformation of the region of the flexible member surrounding the cavity section, the channel can be opened and closed and the flow rate can be regulated. Furthermore, the inventors also discovered that by providing a convex structure on the outer surface of the member corresponding with the cavity section, as a mechanism for selectively compressing the cavity section, the opening and closing of the channel and the flow rate regulation can be performed with ease, and that by forming the members from a radiation-curable resin composition, and then incorporating an amphipathic radiation-curable compound within the resin, a micro chemical device with superior adhesion between members, and low adsorption of biological constituents can be produced with relative ease, and they were consequently able to complete the present invention.

In other words, the present invention provides:

(1) a micro chemical device with a valve function, in which a member (B) is bonded to a member (A) with a groove in the surface thereof, via the surface of the member (A) in which the groove is formed, a capillary type channel of width from 1 to 1000 µm and height from 1 to 1000 µm is formed by the groove of the member (A) and the member (B) at the bonding surface between the member (A) and the member (B), a cavity section is formed partway along the channel and the width of this cavity section is from 0.5 to 100 fold the width of the capillary type channel and the ratio of maximum height/maximum width for the cavity section is no more than 1, and either one of the member (A) and the member (B) is formed from a soft material with a tensile modulus of elasticity within a range from 0.1 MPa to 700 MPa, at least within the portion which corresponds with the position of the cavity section, wherein by selectively compressing the cavity section from the external surface of the member (A) and/or the member (B), the volume of the cavity section can be reduced in a reversible manner.

In addition, the present invention also provides:

(2) a micro chemical device according to (1), wherein either one of the member (A) and the member (B) is formed from a soft material with a tensile modulus of elasticity within a range from 0.1 MPa to 700 MPa, at least within the portion which corresponds with the position of the cavity section, and the other member is formed from a medium hard material with a tensile modulus of elasticity of at least 700 MPa, at least within the region surrounding the cavity section, (3) a micro chemical device according to either one of (1) and (2), wherein at least one of the member (A) and the member (B) is a sheet type member, (4) a micro chemical device according to any one of (1) through (3), wherein a sheet type member (E) formed from a medium hard material with a tensile modulus of elasticity within a range from 700 MPa to 10 GPa, and with a thickness within a range from 0.5 to 500 µm, is laminated to the outside of the member from which the cavity section is compressed from externally, at least within the portion which corresponds with the cavity section, (5) a micro chemical device according to any one of (1) through (4), wherein a convex structure is provided on the member from which the cavity section is compressed, in a position corresponding with the cavity section, (6) a micro chemical device according to any one of (1) through (4), wherein a member (H) with a convex structure is laminated to the outside of the member from which the cavity section is compressed, and the convex structure is fixed in a position corresponding with the cavity section, with the convex structure facing the cavity section, (7) a micro chemical device according to (6), wherein the member (H) with a convex structure is a sheet type member with a convex structure, (8) a micro chemical device according to either one of (6) and (7), wherein the member (H) with a convex structure is laminated on top of either the member (B) or the member (E) with the convex structure facing away from the member (B), and is formed from a material with a tensile modulus of elasticity within a range from 10 MPa to 10 GPa, and with a thickness within a range from 0.5 to 500 μm, (9) a micro chemical device according to any one of (5) through (8), wherein the convex structure is formed from a hard material with a tensile modulus of elasticity of at least 700 MPa,

(10) a micro chemical device according to any one of (1) through (9), wherein the soft material with a tensile modulus of elasticity within a range from 0.1 to 700 MPa, and/or the medium hard material with a tensile modulus of elasticity within a range from 700 MPa to 10 GPa are cured products of radiation-curable compositions, and

(11) a micro chemical device according to (10), wherein the radiation-curable composition comprises an amphipathic radiation-curable compound.

Furthermore, the present invention also provides:

(12) a micro chemical device with a valve function, in which by bonding a member (B) and a member (C) together with a layer type member (D) comprising a lacking section for forming a channel disposed therebetween, a capillary type channel of width from 1 to 1000 μm and height from 1 to 1000 μm is formed between the member (B) and the member (C) by the lacking section of the material of the member (D), and a cavity section is formed partway along the channel and the width of this cavity section is from 0.5 to 100 fold the width of the capillary type channel and the ratio of maximum height/maximum width for the cavity section is no more than 1, and any one of the members (B), (C) and (D) is formed from a soft material with a tensile modulus of elasticity within a range from 0.1 MPa to 700 MPa, at least within the portion which corresponds with the cavity section (or in the case of the member (D), the portion surrounding the cavity section), and any one of the members (B), (C) and (D) is formed from a medium hard material or a hard material with a tensile modulus of elasticity of at least 700 MPa, wherein by compressing the cavity section from the external surface of the member (B), the volume of the cavity section can be reduced in a reversible manner.

In addition, the present invention also provides:

(13) a micro chemical device according to (12), wherein the member (B) is formed from a soft material with a tensile modulus of elasticity within a range from 0.1 MPa to 700 MPa, at least within the portion which corresponds with the cavity section, and the minimum thickness of the portion which corresponds with the cavity section is within a range from 10 to 3000 μm,

(14) a micro chemical device according to (12), wherein the member (B) is formed from a medium hard material with a tensile modulus of elasticity within a range from 700 MPa to 10 GPa, at least within the portion which corresponds with the cavity section, and the minimum thickness of this portion which corresponds with the cavity section is within a range from 0.5 to 500 μm,

(15) a micro chemical device according to any one of (12) through (14), wherein a sheet type member (E) formed from a medium hard material with a tensile modulus of elasticity within a range from 700 MPa to 10 GPa, and with a thickness within a range from 0.5 to 500 μm, is laminated to the outside of the member (B), at least within the portion which corresponds with the cavity section,

(16) a micro chemical device according to any one of (12) through (15), wherein a convex structure is provided on the surface of the member (B), in a position corresponding with the cavity section,

(17) a micro chemical device according to any one of (12) through (15), wherein a member (H) with a convex structure is laminated onto either the member (B) or the member (E), and the convex structure is fixed in a position corresponding with the cavity section with the convex structure facing the cavity section,

(18) a micro chemical device according to (17), wherein the member (H) with a convex structure is a sheet type member with a convex structure,

(19) a micro chemical device according to (16), wherein the member (H) with a convex structure is laminated on top of either the member (B) or the member (E), with the convex structure facing away from the member (B) and with the positional relationship relative to the member (B) fixed so that the convex structure is in a position corresponding with the cavity section, and is formed from a material with a tensile modulus of elasticity within a range from 10 MPa to 10 GPa, and with a thickness within a range from 0.5 to 500 μm,

(20) a micro chemical device according to any one of (12) through (19), wherein the convex structure is formed from a hard material with a tensile modulus of elasticity of at least 700 MPa,

(21) a micro chemical device according to any one of (12) through (20), wherein the soft material with a tensile modulus of elasticity within a range from 0.1 to 700 MPa is a cured product of a radiation-curable composition,

(22) a micro chemical device according to any one of (12) through (21), wherein the medium hard material with a tensile modulus of elasticity within a range from 700 MPa to 10 GPa is a cured product of a radiation-curable composition, and

(23) a micro chemical device according to either one of (21) and (22), wherein the radiation-curable composition comprises an amphipathic radiation-curable compound.

In addition, the present invention also provides:

(24) a micro chemical device with a valve function, in which a member (B) is bonded to a member (A) with a groove in the surface thereof, via the surface of the member (A) in which the groove is formed, a capillary type channel of width from 1 to 1000 μm and height from 1 to 1000 μm is formed by the groove of the member (A) and the member (B) at the bonding surface between the member (A) and the member (B), a cavity section is formed partway along the channel and the width of this cavity section is from 0.5 to 100 fold the width of the capillary type channel and the ratio of maximum height/maximum width for the cavity section is no more than 1, and both the member (A) and the member (B) are formed from a soft material with a tensile modulus of elasticity within a range from 0.1 MPa to 700 MPa, at least within the portion which corresponds with the cavity section, and a convex structure is provided on the surface of the member (A) and/or the member (B), in a position corresponding with the cavity section, wherein by compressing the cavity section from the external surface of the member on which the convex structure is provided, the volume of the cavity section can be reduced in a reversible manner,

(25) a micro chemical device with a valve function, in which a member (B) is bonded to a member (A) with a groove in the surface thereof, via the surface of the member (A) in which the groove is formed, a capillary type channel of width from 1 to 1000 μm and height from 1 to 1000 μm is formed by the groove of the member (A) and the member (B) at the bonding surface between the member (A) and the member (B), a cavity section is formed partway along the channel and the width of this cavity section is from 0.5 to 100 fold the width of the capillary type channel and the ratio of maximum height/maximum width for the cavity section is no more than 1, and both the member (A) and the member (B) are formed from a soft material with a tensile modulus of elasticity within a range from 0.1 MPa to 700 MPa, at least within the portion which corresponds with the cavity section, and a member (H) with a convex structure is laminated onto the member (A) and/or the member (B), or alternatively is laminated onto a sheet type member (E) with a thickness from 0.5 to 500 atm, which is formed from a medium hard material with a tensile modulus of elasticity within a range from 700 MPa to 10 GPa provided on the outside of the member (A) and/or the member (B), and the convex structure is fixed in a position corresponding with the cavity section, wherein by compressing the cavity section from the surface of the member with the convex structure, the volume of the cavity section can be reduced in a reversible manner,

(26) a micro chemical device with a valve function, in which by bonding a member (B) and a member (C) together with a layer type member (D) comprising a lacking section for forming a channel disposed therebetween, a capillary type channel of width from 1 to 1000 μm and height from 1 to 1000 μm is formed between the member (B) and the member (C) by the lacking section of the material of the member (D), and a cavity section is formed partway along the channel and the width of this cavity section is from 0.5 to 100 fold the width of the capillary type channel and the ratio of maximum height/maximum width for the cavity section is no more than 1, and each of the members (B), (C) and (D) is formed from a soft material with a tensile modulus of elasticity within a range from 0.1 MPa to 700 MPa, at least within the portion which corresponds with the cavity section (or in the case of the member (D), the portion surrounding the cavity section), and a convex structure is provided on the surface of the member (B) in a position corresponding with the cavity section, wherein by compressing the cavity section from the surface of the member (B), the volume of the cavity section can be reduced in a reversible manner, and

(27) a micro chemical device with a valve function, in which by bonding a member (B) and a member (C) together with a layer type member (D) comprising a lacking section for forming a channel disposed therebetween, a capillary type channel of width from 1 to 1000 μm and height from 1 to 1000 μm is formed between the member (B) and the member (C) by the lacking section of the material of the member (D), and a cavity section is formed partway along the channel and the width of this cavity section is from 0.5 to 100 fold the width of the capillary type channel and the ratio of maximum height/maximum width for the cavity section is no more than 1, and each of the members (B), (C) and (D) is formed from a soft material with a tensile modulus of elasticity within a range from 0.1 MPa to 700 MPa, at least within the portion which corresponds with the cavity section (or in the case of the member (D), the portion surrounding the cavity section), and a member (H) with a convex structure is laminated onto the member (B), or alternatively is laminated onto a sheet type member (E) with a thickness from 0.5 to 500 μm, which is formed from a medium hard material with a tensile modulus of elasticity within a range from 700 MPa to 10 GPa provided on the outside of the member (B), and the convex structure is fixed in a position corresponding with the cavity section, wherein by compressing the cavity section from the surface of the member (B), the volume of the cavity section can be reduced in a reversible manner.

In addition, the present invention also provides:

(28) a micro chemical device flow regulation method, wherein by selectively compressing a cavity section of a micro chemical device according to any one of (1) through (27) above from externally, the volume of the cavity section within the micro chemical device can be reduced in a reversible manner, and the flow rate of a fluid passing through the cavity section can be regulated, and

(29) a micro chemical device flow regulation method according to (27), wherein by selectively compressing the cavity section from externally, the flow rate of the fluid passing through the cavity section can be reduced to zero.

BEST MODE FOR CARRYING OUT THE INVENTION

Figure 1A:
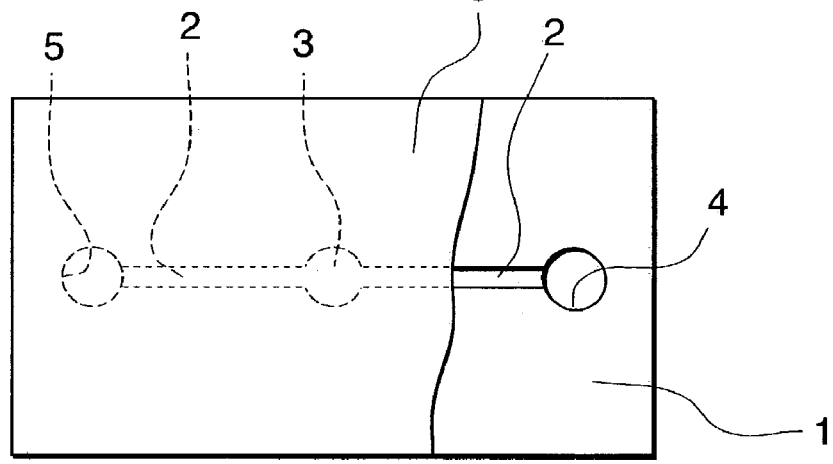
FIG. 1 is a schematic illustration of a partial sectional plan view A, and a schematic illustration of an elevation B, of a micro chemical device prepared in an example 1.

A micro chemical device of the present invention comprises a member (A) and a member (B) which are bonded together, and a capillary type channel (hereafter, the term "capillary type channel" may be abbreviated as simply "channel") is formed between the two members. By bonding the member (B) to the surface of the member (A) in which the groove is formed, the channel is formed by the groove and the member (B), and if the member (A) is on the lower side (hereafter, the terms "up", "down" and "height" used in relation to a micro chemical device of the present invention formed from a member (A) and a member (B) describe this situation), then the bottom surface and the side surfaces of the channel are formed by the member (A), and the upper surface of the channel is formed by either the member (B) or an adhesive applied to the member (B).

When viewed from above, that is, from a direction perpendicular to the bonding surface between the member (A) and the member (B), the channel has a width of at least 1 µm, and preferably at least 10 µm, and furthermore no more than 1000 µm, and preferably no more than 500 µm. The height of the channel is at least 1 µm, and preferably at least 10 µm, and furthermore is no more than 1000 µm, and preferably no more than 500 µm. If the dimensions of the channel are smaller than the above ranges then production becomes problematic. Furthermore, if the dimensions of the channel are larger than the above ranges then the effects of the present invention tend to decrease, which is undesirable. The ratio of the width/depth of the channel can be set as desired in accordance with the intended application or purpose, although typically a ratio within a range from 0.5 to 10 is preferred, and ratios from 0.7 to 5 are even more desirable. The cross sectional shape of the channel is arbitrary and may be rectangular (including rectangles with rounded corners. Hereafter, this definition continues to apply), trapezoidal, circular or hemispherical. In the present invention, the width of the channel refers to the maximum width of the channel cross section. The width of the channel need not necessarily be constant.

The shape of the channel when viewed from above is arbitrary and may be linear, branched, comb shaped, curved, a spiral, a zigzag, or any other shape, depending on the purpose of the application. In addition to functioning as a channel, the channel may also be used as a reaction site, a mixing site, an extraction site, a separation site, a flow rate measurement section, or a detection section or the like, and other structures which connect to the channel, such as fluid storage vessels, reaction vessels, membrane separation mechanisms or external connection ports or the like, may also be formed.

The groove formed in the member (A) may be formed as a groove which is lower than the surrounding sections, or may also be formed between walls which stand up off the surface of the member (A). The method of forming the groove in the surface of the member (A) is arbitrary, and suitable methods which can be used include injection molding, solvent casting methods, molten replication methods, cutting, photolithography (including radiation lithography), etching methods, vapor deposition methods, vapor phase polymerization methods, and methods in which a sheet type member in which a section which is to become the groove has been cut out and removed is bonded to a flat member. The member (A) may be formed from a plurality of materials, so that, for example, the bottom and the side walls of the groove may be formed from different materials. Structural sections other than the groove, such as fluid storage vessels, reaction vessels, or structures which function as analysis mechanisms, may also be provided in the member (A).

There are no particular restrictions on the shape of the member (A), and the shape can be selected in accordance with the purpose of the application. The shape of the member (A) may be a sheet (including films and ribbons and the like. Hereafter, this definition continues to apply), a flat board, a coating film, a rod, a tube, or a variety of other more complex formed shapes, although from the viewpoint of ensuring good ease of bonding with the member (B), the bonding surface is preferably flat, and sheets, flat boards or rods are particularly preferred. In those cases in which compression is applied from the side of the member (A), devices in which the member (A) is a sheet are particularly preferred. The member (A) may also be formed on top of a base material. The base material is preferably formed from a hard material with a tensile modulus of elasticity of at least 700 MPa. A plurality of micro chemical devices can also be formed on the member (A), and following production, the member (A) can then be cut up to form a plurality of separate micro chemical devices.

The member (B) is bonded to the member (A) with a groove in the surface via the surface of the member (A) in which the groove is formed, and provided a capillary type channel can be formed using the groove of the member (A) and the member (B), there are no particular restrictions on the shape, structure or surface form of the member (B). These factors can be selected in a similar manner to the member (A). The member (B) need not have a groove in the surface, although the member (B) may also comprise a groove or other structures. For example, the member (B) may be a mirror image of the member (A) with a groove in the surface, or the groove formed in the member (A) may partially overlap with a groove formed in the member (B), forming a connected channel.

The method for bonding the member (A) with the groove in the surface and the member (B) may be any method provided the groove in the surface of the member (A) forms a capillary type channel, and suitable methods include using a solvent based adhesive, using a solvent free adhesive, using a molten adhesive, applying a solvent to the surface of the member (A) and/or the member (B), and using fusion achieved by either heat or ultrasound, although using a solvent free adhesive is preferred. Amongst solvent free adhesives, bonding methods using a radiation-curable composition, in which curing and bonding are achieved by irradiation with a radiation, can be used for the precise bonding required for a micro chemical device, and also offer good productivity, and are consequently preferred. Furthermore, a method in which the member (A) and/or the member (B) are formed as semi cured products of a radiation-curable composition, and final curing and bonding is then achieved by further irradiation with a radiation once the members are in contact with each other, is also preferred.

A micro chemical device of the present invention comprises a cavity section formed partway along the channel. In other words, the cavity section is provided in a position which if closed, blocks off the channel. With the member (A) on the bottom, and lying in the horizontal plane, if the height and width of the cavity section in a cross section at right angles to the direction of the channel are used to describe the height and width respectively of the cavity section, and the length of the cavity section in the direction of the channel within a plane parallel to the bonding surface between the member (A) and the member (B) is used to describe the length of the cavity section, then the width of the cavity section is at least 0.5 fold, and preferably at least 0.7 fold, and furthermore no more than 100 fold, and preferably no more than 10 fold, and even more preferably no more than 3 fold the width of the capillary type channel. If the width of the cavity section is narrower than the above range then the pressure loss within the channel increases, whereas if the width is greater than the above range then the dead volume of the valve section increases and the fluid movement during the opening and closing of the valve or the regulation of the flow rate increases, which is undesirable.

In addition, the maximum height/maximum width ratio for the cavity section is preferably no more than 1. If the maximum height/maximum width ratio exceeds 1, then completely closing the valve, namely the cavity section, becomes difficult. From the viewpoint of ease of production, the height of the cavity section is preferably the same as the height of the channel. There is no particular requirement to restrict the length of the cavity section. Accordingly, provided the above dimensional requirements are satisfied, the cavity section may even be the capillary type channel itself. In those cases in which the cavity section is long, the compression region described below may be only one portion of the cavity section. However, in cases in which the width of the cavity section becomes greater than the width of the capillary type channel, the maximum length/maximum width ratio of the cavity section is preferably at least 0.7. In such cases, if the length of the cavity section is shorter than this requirement, then completely closing the valve becomes difficult. The cavity section is preferably of the same width or wider than the width of the capillary type channel, and of the same height or shallower than the height of the channel.

A plurality of cavity sections may exist within a micro chemical device of the present invention, and by providing a plurality of cavity sections, a plurality of valve functions can be provided within the micro chemical device.

The shape of the cavity section is arbitrary, provided the dimensions of the cavity section fall within the ranges described above, and the shape of the cavity section when viewed from a direction perpendicular to the bonding surface between the member (A) and the member (B) may be circular, elliptical, polygonal or rectangular, for example. Of these shapes, circular or rectangular shapes are preferred as they are easier to produce and also easier to close completely. Furthermore, the cross sectional shape of the cavity section when viewed from a direction parallel to the bonding surface between the member (A) and the member (B) may be rectangular, a circular cone or a pyramid, circular or elliptical, or hemispherical, although rectangular shapes are easier to produce and consequently preferred.

In a first embodiment of a micro chemical device of the present invention, a portion of either one of the member (A) and the member (B) which opposes and contacts the cavity section, in other words, the portion which forms the bottom and/or the ceiling of the cavity section, (hereafter, this portion is termed the "portion corresponding with the cavity section") is formed from a material with a tensile modulus of elasticity (or in the case of materials for which the tensile modulus of elasticity is difficult to measure, a bending modulus of elasticity) within a range from 0.1 to 700 MPa, and preferably from 1 to 400 MPa [hereafter, this type of material is described as a "soft material (s)"] [hereafter, a member in which the portion which opposes and contacts the cavity section is formed from a soft material (s) is described as a "member formed from a soft material (s)"]. If the modulus of elasticity exceeds the above range, then regulation of the flow rate becomes difficult, and the device tends to be prone to breakage at the valve section. A suitable tensile modulus of elasticity also depends on factors such as the shape of the cavity section, and the thickness of the portion corresponding with the cavity section formed from the soft material (s), and as the height of the cavity section reduces and the thickness of the portion corresponding with the cavity section becomes thinner, a material with a comparatively higher tensile modulus of elasticity should preferably be used. The lower limit for the tensile modulus of elasticity can be very small, provided the material is a self supporting solid, although from the viewpoint of ease of handling, this lower limit is at least 0.1 MPa, and preferably at least 1 MPa, and even more preferably 10 MPa or greater.

The lower the value of the tensile modulus of elasticity, the easier complete closure of the valve becomes, although in cases where strength or pressure resistance are required, or in cases where the thickness of the portion formed from the soft material (s) is reduced, a material with a comparatively high tensile modulus of elasticity should preferably be used.

The portion formed from the soft material (s) comprises at least the portion which opposes and contacts the cavity section, although a larger portion which also includes this portion corresponding with the cavity section is preferably formed using the soft material, and in terms of ease of production, the member (A) or the member (B) is preferably formed entirely from the soft material (s).

In a micro chemical device according to the present invention, formed from a member (A) and a member (B), at least the portion corresponding with the cavity section within the other member which is not formed from the soft material (s) is formed either from a material with a tensile modulus of elasticity within a range from 700 MPa to 10 GPa, and preferably from 1 to 5 GPa [hereafter, this type of material is described as a "medium hard material (m)"], or alternatively from a material with a tensile modulus of elasticity exceeding 10 GPa [hereafter, this type of material is described as a "hard material (h)"] [hereafter, a member in which at least the portion corresponding with the cavity section is formed from a medium hard material (m) is described as a "member formed from a medium hard material (m)", and a member in which at least the portion corresponding with the cavity section is formed from a hard material (h) is described as a "member formed from a hard material (h)"]. By employing such a structure, the thickness of the device can be kept relatively thin, while a high level of pressure resistance can be imparted, and the degrees of freedom increase for the method of compressing the cavity section and regulating the flow rate. Moreover, cases in which the member on the side used to compress the cavity section is formed from either a soft material (s) or a medium hard material (m) are possible, although suitable thickness values for each member in these cases are described below in the sections relating to preferred embodiments.

The soft material (s) preferably has a breaking elongation of at least 5%, and even more preferably at least 10%. In those cases where a valve mechanism of the present invention is used in an application that requires repeated opening and closing of the valve, it is particularly desirable that the breaking elongation satisfies the above requirement. However, in methods of using an embodiment of the present invention where the soft material (s) is subjected to deformation, even materials which display a low value in a tensile test according to JIS (such as JIS K-7127) are still unlikely to break, and even if a distortion is applied which exceeds the breaking elongation according to the above test, in many cases the material does not break and remains usable.

The soft material (s) used in the present invention may be any material which is impermeable to the fluid used in a micro chemical device of the present invention, and also possesses sufficient strength to not break during use of the micro chemical device of the present invention. The soft material (s) is preferably an organic high molecular weight polymer (hereafter described simply as a "polymer"). This polymer may be a homopolymer or a copolymer, and may be either a thermoplastic polymer or a thermosetting polymer. In terms of productivity, the polymer is preferably a thermoplastic polymer or a cured product of a radiation-curable composition.

There are no particular restrictions on the polymers which can be used as the soft material (s), although examples of preferred polymers include rubbers such as silicon rubber, (substituted) isoprene type rubbers, (substituted) butadiene type rubbers and nitrile rubber; polyolefin based polymers such as polyethylene and modified polyolefins; chlorine containing polymers such as polyvinyl chloride and polyvinylidene chloride; vinyl acetate based polymers; polyurethane based polymers; polyamide based polymers; polyester based polymers; epoxy resins; and copolymers of the above.

Even if a polymer has a tensile modulus of elasticity outside the prescribed range as a homopolymer, the polymer can still be used by appropriate blending with a plasticizer or another polymer, or by conversion to an appropriate copolymer.

The polymers which can be used as the soft material (s) are also preferably cured products of radiation-curable compositions. Radiation-curable compositions comprise a radiation-curable compound as an essential constituent, and may comprise either a single radiation-curable compound or a mixture of a plurality of different radiation-curable compounds. In order to improve the strength, the radiation-curable composition preferably forms a cross linked polymer. In order to ensure that the cured product of the radiation-curable composition is a cross linked polymer, polyfunctional monomers and/or oligomers can be incorporated within the radiation-curable composition. In order to enable regulation of the tensile modulus of elasticity and improvement of the adhesion, the radiation-curable composition is preferably a mixture of monofunctional monomers and/or oligomers.

The radiation-curable compound of the radiation-curable composition may be a radical polymerizable, anionic polymerizable, or cationic polymerizable compound. The radiation-curable compounds are not restricted to compounds which polymerize without the presence of a polymerization initiator, and compounds which polymerize under irradiation with a radiation only in the presence of a polymerization initiator can also be used. This type of radiation-curable compound preferably comprises a polymerizable carbon-carbon double bond, and of such compounds, highly reactive (meth)acrylic based compounds and vinyl ethers are preferred, and compounds with at least two (meth)acryloyl groups within each molecule, or maleimide based compounds which cure even without the presence of a photopolymerization initiator are particularly preferred.

Examples of cross linking polymerizable (meth)acrylic based monomers which can be favorably used as the radiation-curable compound include bifunctional monomers such as diethylene glycol di(meth)acrylate, neopentyl glycol di(meth)acrylate, 1,6-hexanediol di(meth)acrylate, 1,8-octanediol di(meth)acrylate, 2,2'-bis(4-(meth)acryloyl oxypolyethyleneoxyphenyl)propane, 2,2'-bis(4-(meth)acryloyl oxypolypropyleneoxyphenyl)propane, hydroxydipivalic acid neopentyl glycol (meth)acrylate, dicyclopentanyl diacrylate, bis(acryloxyethyl)hydroxyethyl isocyanurate and N-methylenebisacrylamide; trifunctional monomers such as trimethylolpropane tri(meth)acrylate, trimethylolethane tri (meth)acrylate, tris(acryloxyethyl) isocyanurate and caprolactone modified tris(acryloxyethyl) isocyanurate; tetrafunctional monomers such as pentaerythritol tetra(meth)acrylate; and hexafunctional monomers such as dipentaerythritol hexa(meth)acrylate.

Furthermore, polymerizable oligomers (also known as prepolymers) may also be used as a radiation-curable compound, including oligomers with a weight average molecular weight within a range from 500 to 50,000. Examples of this type of polymerizable oligomer include (meth)acrylate esters of epoxy resins, (meth)acrylate esters of polyether resins, (meth)acrylate esters of polybutadiene resins and polyurethane resins with (meth)acryloyl groups at the molecular terminals.

Examples of maleimide based cross linking polymerizable radiation-curable compounds include bifunctional maleimides such as 4,4'-methylenebis(N-phenylmaleimide), 2,3-bis(2,4,5-trimethyl-3-thienyl)maleimide, 1,2-bismaleimidoethane, 1,6-bismaleimidohexane, triethylene glycol bismaleimide, N,N'-m-phenylenedimaleimide, m-tolylenedimaleimide, N'N'-1,4-phenylenedimaleimide, N,N'-diphenylmethanedimaleimide, N,N'-diphenyletherdimaleimide, N,N'-diphenylsulfonedimaleimide, 1,4-bis(maleimidoethyl)-1,4-diazoniabicyclo[2,2,2]octane dichloride and 4,4'-isopropylidenediphenyl dicyanato•N,N'-(methylenedi-p-phenylene)dimaleimide; and maleimides with a maleimide group and another non-maleimide polymerizable functional group such as N-(9-acridinyl)maleimide.

Examples of maleimide based cross linking polymerizable oligomers include polytetramethylene glycol maleimidoalkylates such as polytetramethylene glycol maleimidocaprylate and polytetramethylene glycol maleimidoacetate.

Maleimide based monomers and oligomers can be polymerized together, and/or can be copolymerized with a compound comprising a polymerizable carbon-carbon double bond such as a vinyl monomer, a vinyl ether or an acrylic based monomer.

These compounds can be used singularly, or in mixtures of two or more different compounds. Amongst the compounds listed above, some compounds may yield a cured product with a tensile modulus of elasticity outside the prescribed range if polymerized as a single compound, although by using such compounds in mixtures with other copolymerizable compounds including monofunctional monomers such as monofunctional (meth)acrylic monomers, or with non-reactive compounds such as plasticizers, these compounds can also be used.

The radiation-curable composition preferably comprises an amphipathic polymerizable compound which is copolymerizable with the radiation-curable compound which is the main essential constituent of the radiation-curable composition. By incorporating an amphipathic compound, the cured product of the composition is less likely to swell in water, and is moreover hydrophilic, enabling the formation of a surface which displays low adsorption relative to biochemical matter. The amphipathic polymerizable compound comprises both a hydrophilic group and a lipophilic group within the molecule, and incorporates a polymerizable functional group capable of undergoing copolymerization with the radiation-curable compound of the radiation-curable composition on irradiation with an activating radiation. In cases in which the radiation-curable compound is a compound comprising at least two polymerizable carbon-carbon unsaturated bonds within each molecule, the amphipathic polymerizable compound is preferably a compound with at least one polymerizable carbon-carbon unsaturated bond within each molecule. The amphipathic polymerizable compound need not necessarily form a cross linked polymer, although compounds which form a cross linked polymer are also suitable.

The amphipathic polymerizable compound is also a compound which is mutually and uniformly soluble with the radiation-curable compound. In this case, the term "soluble" describes a state in which macroscopic phase separation does not occur, and includes states in which a micelle forms and a stable dispersion is produced.

The amphipathic polymerizable compound comprises both a hydrophilic group and a lipophilic group within each molecule, and is mutually soluble with both water and lipophilic solvents. In this case, as above, the term "soluble" describes a state in which macroscopic phase separation from the solvent does not occur, and includes states in which a micelle forms and a stable dispersion is produced. The amphipathic polymerizable compound preferably has a solubility in water at 0° C. of at least 0.5% by weight, and a solubility in a mixed solvent of cyclohexane:toluene=5:1 (weight ratio) at 25° C. of at least 25% by weight.

In this description, the term "solubility", for example in the case of a solubility of at least 0.5% by weight, describes a state in which at least 0.5% by weight of the compound is soluble, and does not include the case in which 0.5% by weight of the compound is not soluble in the solvent but a very small quantity of the solvent is soluble within the compound. If a compound is used for which at least one of the solubility in water or the solubility in a mixed solvent of cyclohexane:toluene=5:1 (weight ratio) is lower than the values above, then satisfying the requirements for both a high surface hydrophilicity and a high water resistance becomes difficult.

In those cases in which the amphipathic polymerizable compound comprises a nonionic hydrophilic group, particularly a polyether based hydrophilic group, the balance between hydrophilicity and lipophilicity is preferably a Griffin HLB value within a range from 11 to 16, and even more preferably from 11 to 15. At values outside this range, it either becomes difficult to obtain a formed product with a high hydrophilicity and superior water resistance, or the combination and mixing ratios of compounds required to form the product are extremely restrictive, and the properties of the formed product tend to be unstable.

There are no particular restrictions on the hydrophilic group of the amphipathic polymerizable compound, and suitable examples include cationic groups such as amino groups, quaternary ammonium groups and phosphonium groups; anionic groups such as sulfone groups, phosphoric acid groups and carbonyl groups; nonionic groups such as hydroxyl groups, polyethylene glycol groups and amide groups; and amphoteric ions such as amino acid groups. The amphipathic polymerizable compound is preferably a compound with a polyether group as the hydrophilic group, and compounds with a polyethylene glycol chain with 6 to 20 repeating units are particularly preferred.

Examples of the lipophilic group of the amphipathic polymerizable compound include alkyl groups, alkylene groups, alkylphenyl groups, long chain alkoxy groups, fluorine substituted alkyl groups and siloxane groups.

The amphipathic polymerizable compound is preferably a compound with an alkyl group or alkylene group of 6 to 20 carbon atoms as the lipophilic group. The alkyl group or alkylene group of 6 to 20 carbon atoms may also be included in the form of an alkylphenyl group, an alkylphenoxy group, an alkoxy group or a phenylalkyl group or the like.

The amphipathic polymerizable compound is preferably a compound with a polyethylene glycol chain with 6 to 20 repeating units as the hydrophilic group, and an alkyl group or an alkylene group of 6 to 20 carbon atoms as the lipophilic group.

Of these amphipathic polymerizable compounds, nonylphenoxypolyethylene glycol (n=8 to 17) (meth)acrylate and nonylphenoxypolypropylene glycol (n=8 to 17) (meth)acrylate are particularly preferred.

The preferred ratio between the radiation-curable compound and the amphipathic polymerizable compound will vary depending on the variety and the combination of the radiation-curable compound and the amphipathic polymerizable compound, although at least 0.1 parts by weight, and preferably at least 0.2 parts by weight of the amphipathic polymerizable compound should be included per 1 part by weight of the other radiation-curable compound. At values less than the above range, the formation of a highly hydrophilic surface becomes difficult.

Furthermore, the proportion of the amphipathic polymerizable compound is preferably no more than 5 parts by weight, and even more preferably less than 3 parts by weight per 1 part by weight of the other radiation-curable compound. If the quantity of the amphipathic polymerizable compound relative to 1 part by weight of the radiation-curable compound exceeds 5 parts by weight, then the product tends to be prone to swelling in the presence of water, and the polymer within the wetted portion tends to be prone to gelling.

By appropriate selection of the mixing ratio of the radiation-curable compound and the amphipathic polymerizable compound, a cured product can be produced which does not gel in wet conditions, and displays high hydrophilicity and low adsorption. As the relative strength of the hydrophilicity of the amphipathic polymerizable compound increases, for example as the HLB value increases, the preferred addition quantity of that compound decreases.

Where necessary, a photopolymerization initiator may also be added to the radiation-curable compound. There are no particular restrictions on the photopolymerization initiator, provided the initiator is active relative to the radiation used, and enables the polymerization of the radiation-curable compound, and radical polymerization initiators, anionic polymerization initiators and cationic polymerization initiators are all possible. The photopolymerization initiator may also be a maleimide compound.

Examples of usable monofunctional maleimide based monomers include N-alkyl maleimides such as N-methylmaleimide, N-ethylmaleimide, N-butylmaleimide and N-dodecylmaleimide; N-alicyclic maleimides such as N-cyclohexylmaleimide; N-benzylmaleimide; N-(substituted or unsubstituted phenyl)maleimides such as N-phenylmaleimide, N-(alkylphenyl)maleimide, N-dialkoxyphenylmaleimide, N-(2-chlorophenyl)maleimide, 2,3-dichloro-N-(2,6-diethylphenyl)maleimide and 2,3-dichloro-N-(2-ethyl-6-methylphenyl)maleimide; halogen containing maleimides such as N-benzyl-2,3-dichloromaleimide and N-(4'-fluorophenyl)-2,3-dichloromaleimide; hydroxyl group containing maleimides such as hydroxyphenylmaleimide; carboxy group containing maleimides such as N-(4-carboxy-3-hydroxyphenyl)maleimide; alkoxy group containing maleimides such as N-methoxyphenylmaleimide; amino group containing maleimides such as N-[3-(diethylamino)propyl]maleimide; polycyclic aromatic maleimides such as N-(1-pyrenyl)maleimide; and heterocyclic maleimides such as N-(dimethylamino-4-methyl-3-coumarinyl)maleimide and N-(4-anilino-1-naphthyl)maleimide.

Suitable examples of the radiation include light beams such as ultraviolet light beams, visible light beams and infrared light beams; ionizing radiation such as X-rays and gamma rays; and particle beams such as electron beams, ion beams, beta rays and heavy particle beams.

Furthermore, the soft material (s) may also be a polymer blend or a polymer alloy, or a foam, a layered product or another type of complex. In addition, the soft material (s) may also comprise other constituents such as modifiers or coloring agents.

Examples of modifiers which can be incorporated within the soft material (s) include anionic, cationic and nonionic surfactants, inorganic powders such as silica gel, hydrophilic agents including hydrophilic polymers such as polyvinyl pyrrolidone, and plasticizers such as dioctyl phthalate. Examples of coloring agents which can be incorporated within the soft material (s) include any dye or pigment, fluorescent dyes or pigments, and ultraviolet absorbers.

A medium hard material (m) has a tensile modulus of elasticity within a range from 700 MPa to 10 GPa, and preferably from 1 to 5 GPa, and can be any material which possesses sufficient strength to not break during use of the micro chemical device of the present invention, although is preferably a polymer. Polymers which can be used as the medium hard material (m) include homopolymers and copolymers, and may be either thermoplastic polymers or thermosetting polymers. In terms of productivity, the polymer is preferably a thermoplastic polymer or a cured product of a radiation-curable composition.

Examples of polymers which can be used as the medium hard material (m) include styrene based polymers such as polystyrene, poly-α-methylstyrene, copolymers of polystyrene and maleic acid, and copolymers of polystyrene and acrylonitrile; polysulfone based polymers such as polysulfone and polyethersulfone; (meth)acrylic based polymers such as polymethylmethacrylate and polyacrylonitrile; polymaleimide based polymers; polycarbonate based polymers such as bisphenol A based polycarbonate, bisphenol F based polycarbonate and bisphenol Z based polycarbonate; polyolefin based polymers such as polyethylene, polypropylene and poly-4-methylpentene-1; chlorine containing polymers such as polyvinyl chloride and polyvinylidene chloride; cellulose based polymers such as cellulose acetate and methylcellulose; polyurethane based polymers; polyamide based polymers; polyimide based polymers; fluorine based polymers; polyether or polythioether based polymers such as poly-2,6-dimethylphenylene oxide and polyphenylene sulfide; polyetherketone based polymers such as polyetheretherketone; polyester based polymers such as polyethylene terephthalate and polyarylate; epoxy resins; urea resins; and phenol resins. Of these, styrene based polymers, (meth) acrylic based polymers, polycarbonate based polymers, polysulfone based polymers and polyester based polymers are preferred as they offer superior adhesion.

The polymers which can be used as the medium hard material (m) are also preferably cured products of radiation-curable compositions. Radiation-curable compositions comprise a radiation-curable compound as an essential constituent, and may comprise either a single radiation-curable compound or a mixture of a plurality of different radiation-curable compounds. In order to improve the strength and the hardness, the radiation-curable composition preferably forms a cross linked polymer. In order to ensure that the cured product of the radiation-curable composition is a cross linked polymer, polyfunctional monomers and/or oligomers must be incorporated within the radiation-curable composition, although other monofunctional monomers and/or oligomers may also be mixed into the composition. The radiation-curable compound includes not only compounds which can be polymerized without the presence of a radiation polymerization initiator, but also includes compounds which polymerize under irradiation with a radiation only in the presence of a radiation polymerization initiator.

Compounds which comprise a polymerizable carbon-carbon double bond are preferred as the radiation-curable compound, and of such compounds, highly reactive (meth) acrylic based compounds, vinyl ethers, or maleimide based compounds which cure even without a photopolymerization initiator are preferred.

Radiation-curable compounds which can be used as the medium hard material (m) include those compounds listed as suitable compounds for the soft material (s) of the present invention which also yield a cured product with a predetermined tensile modulus of elasticity.

A hard material (h) has a tensile modulus of elasticity of at least 10 GPa, and can be any material which possesses sufficient strength to not break during use of the micro chemical device of the present invention. Although there is, of course, a natural upper limit to the tensile modulus of elasticity, there are no particular problems associated with a high tensile modulus of elasticity, and as such no upper limit need be set. Examples of materials which can be used as the hard material (h) include polymers, glass, crystals such as quartz, carbon, ceramics, semiconductors such as silicon, and metals, although of these, polymers are particularly preferred due to their ease of forming, high productivity, and low cost. Polymers which can be used as the hard material (h) include polymers for which the tensile modulus of elasticity exceeds 10 GPa, with other requirements being the same as for the medium hard material (m).

A compression mechanism for selectively compressing the cavity section of a micro chemical device of the present invention may comprise a structure which is fixed to the micro chemical device and selectively compresses the cavity section of the micro chemical device, or a structure which is separate from the main body of the device. The compression mechanism is a mechanism in which the tip thereof applies a certain arbitrary compression within a dimensional range for compression described above, and examples of the mechanism include a weight, a spring type or a screw type clamp; a screw or spring fixed to the micro chemical device; or an actuator using a motor, an electromagnet or compressed air.

Of these different mechanisms, in those cases in which the device is used as an opening and closing valve, a spring type clamp is the simplest, whereas in those cases in which the device is used as a flow rate regulation valve, an adjustable screw provided on a separate member fixed to the micro chemical device is ideal. There are no particular restrictions on the shape or dimensions of this member on which the screw is provided, and for example, the member may be a structure which entirely covers the member with a portion formed from the soft material (s), or may be fixed only on the portion at which compression occurs. The material for this member is also arbitrary, and a hard material (h) can be used, for example. In those cases in which the micro chemical device is used for a complex valve switching application such as in an automated synthesis device, the compression mechanism is preferably an actuator. The actuator is also preferably driven under the control of a sequencer or computer.

A micro chemical device comprising a member (A) and a member (B) is preferably provided with a convex structure on the member from which the cavity section is compressed, in a position corresponding with the cavity section. By providing a convex structure, the portion corresponding with the cavity section can be selectively compressed by simply pressing anywhere within a large area incorporating the convex structure. In other words, the problems associated with selectively compressing a very small cavity section can be resolved.

Furthermore, in another micro chemical device comprising a member (A) and a member (B), a member (H) with a convex structure is preferably laminated to the outside of the member from which the cavity section is compressed, and the convex structure is preferably fixed in a position corresponding with the cavity section, with the convex structure facing the cavity section. The member (H) with the convex structure is even more preferably a sheet type member with a convex structure. In such a case, similar effects to those described above can be achieved.

Furthermore, in yet another micro chemical device comprising a member (A) and a member (B), the member (H) with a convex structure is preferably laminated on top of either the member formed from the soft material (s) or the member (E) with the convex structure facing away from the member formed from the soft material (s), and is preferably formed from a material with a tensile modulus of elasticity within a range from 10 MPa to 10 GPa, and with a thickness within a range from 0.5 to 500 µm. This type of structure is also capable of achieving similar effects to those described above. In addition, in the above description, the convex structure is preferably formed from a hard material with a tensile modulus of elasticity of at least 700 MPa. Details regarding this structure are described below in the sections relating to preferred embodiments.

In those cases in which a micro chemical device of the present invention comprises a convex structure, or in cases in which a member (H) is fixed to the device, there are no particular restrictions on the shape or dimensions of the actuation surface of the mechanism for pushing the convex structure. In cases in which the micro chemical device comprises a plurality of cavity sections and a plurality of corresponding convex structures, unnecessary compression of a different convex structure must be avoided, but in all other cases, even if a large area of the member, or in some cases even the entire member, is compressed, only that portion on which the convex structure is provided undergoes deformation, causing an opening and closing of the valve or a regulation of the flow rate. The actuation mechanism for pushing the convex structure is also arbitrary, and may have a flat actuation surface, but otherwise can utilize the same mechanism as that described above for the compression mechanism. For example, possible mechanisms include a weight, a spring type or a screw type clamp; a screw or spring fixed to the micro chemical device; or an actuator using a motor, an electromagnet or compressed air. Preferred forms of this mechanism for pushing the convex structure are similar to those described above for the compression mechanism.

In order to form a micro chemical device of the present invention capable of performing valve opening and closing or flow rate regulation using the type of compression mechanism described above, a material with a high tensile modulus of elasticity can be used instead of the direct actuation using compressed air described in the preceding literature, and furthermore, the thickness of the member can be increased, and consequently a micro chemical device with a high level of pressure resistance can be produced.

As follows is a description of an embodiment of a micro chemical device of the present invention formed from a member (A) and a member (B).

A first preferred embodiment of the present invention is constructed so that compression is performed from the side of either the member (A) or the member (B), which is formed from a soft material (s). The thickness of the portion of the member (A) or the member (B) formed from the soft material (s) which corresponds with the cavity section, at the thinnest portion in those cases in which variation occurs in the thickness, is at least 10 µm, and preferably at least 50 µm, and furthermore no more than 3000 µm, and preferably no more than 1000 µm, and even more preferably no more than 500 µm. If the thickness is too small, then the pressure resistance decreases, and the likelihood of the portion breaking under the type of compression described below increases, whereas if the thickness is overly large, then complete closure becomes difficult. The optimum value for the thickness will also depend on the height of the cavity section, and as the height of the cavity section increases, the thickness of this portion should preferably also increase.

Provided the minimum thickness of the portion of the member formed from the soft material (s) which corresponds with the cavity section falls within the range described above, the shape and dimensions of the other portions are arbitrary, although the member is preferably a sheet type member formed from the soft material (s).

In those cases in which the member formed from the soft material (s) is the member (A), the thickness of the member (A), minus the depth of the concave section which forms the cavity section, is preferably within a range from 10 to 3000 µm. Furthermore, in those cases in which the member formed from the soft material (s) is the member (B), the member (B) is a sheet, and the thickness of the sheet is preferably the same as the width of a soft material (s) portion corresponding with the cavity section, as described above. Of these two cases, the case in which the member (B) is a sheet type member formed from the soft material (s) more readily exhibits the effects of the present invention, and is also easier to manufacture, and is consequently preferred.

The portion corresponding with the cavity section formed from the soft material (s) is also preferably a layered product formed from a plurality of materials with different tensile modulus of elasticity values, with the tensile modulus of elasticity of the overall layered product falling within a range from 0.1 to 700 MPa. In such a case, the layer which contacts the cavity section is preferably formed from a material with a tensile modulus of elasticity of 0.1 to 200 MPa, and the adjacent outer layer is preferably formed from a material with a tensile modulus of elasticity which is higher than the layer which contacts the cavity section but no more than 700 MPa. The tensile modulus of elasticity of the outside layer is preferably within a range from 100 to 700 MPa. By employing this type of layered structure, complete closure of the valve becomes easier, the compression section can be made less prone to breakage, and in addition, the use of an extremely soft material with a tensile modulus of elasticity of 0.1 to 10 MPa is easier, the use of a material with a breaking elongation of less than 5% also becomes easier, and the thickness of the member can be reduced. In cases in which this type of layered product is employed, the thickness of the portion corresponding with the cavity section formed from the soft material (s), or at least the thickness of the layer which contacts the cavity section, is preferably within a range from 10 to 3000 µm, and products in which the thickness of the entire layered product falls within this range are even more preferred.

In the first preferred embodiment of the present invention, a sheet type member (E) formed from a medium hard material (m) with a tensile modulus of elasticity within a range from 700 MPa to 10 GPa, and preferably from 1 GPa to 5 GPa, is preferably laminated to the outside of the portion corresponding with the cavity section formed from the soft material (s). If the tensile modulus of elasticity exceeds the above range then complete closure of the valve becomes difficult, and the opening and closing of only one of a plurality of adjacent valve mechanisms also becomes difficult. The laminated sheet may be either bonded or non-bonded. The thickness of this member (E) is at least 0.5 µm, and preferably at least 5 µm, and is also no more than 500 µm, and preferably no more than 100 µm, and even more preferably no more than 30 μm. The relationship between the tensile modulus of elasticity and the thickness of the member (E) is preferably within a range which displays flexibility of the sheet structure with respect to bending. In other words, as the tensile modulus of elasticity of the material of the member (E) increases, the thickness of the sheet is preferably reduced. The value of "tensile modulus of elasticity×thickness" is preferably within a range from $3×10^{-4}$ to $1×10^{-1}$ MPa·m, and even more preferably within a range from $3×10^{-3}$ to $1×10^{-2}$ MPa·m.

The member (E) is preferably a sheet of uniform thickness. If the thickness of the member is overly thin, then rupture of the layer becomes more likely, whereas in contrast if the layer is overly thick, then complete closure of the valve becomes difficult, and the opening and closing of only one of a plurality of adjacent valve mechanisms also becomes difficult. As the tensile modulus of elasticity of the material which forms the layer increases, the thickness of the layer preferably decreases. By providing this type of layered structure, the use of a soft material (s) with an extremely small tensile modulus of elasticity becomes easier, and consequently complete closure of the valve is easier, the pressure resistance improves, the breaking strength increases, and the thickness of the member can also be reduced.

In those cases in which the member formed from the soft material (s) comprises a convex structure described below on the surface of the portion corresponding with the cavity section, the member (E) can be laminated to the outside of the convex structure either with or without bonding. In such a case, the laminated state of the layer is such that a structure is formed in which a space remains around the periphery of the convex structure, and when the region surrounding the convex structure is compressed from outside the layer, the force is applied selectively to the convex structure section, and the convex structure must not be embedded within the member (E).

The first preferred embodiment of the present invention also preferably comprises a mechanism (a compression mechanism) which selectively compresses the cavity section form the side of the member formed from the soft material (s).

The region compressed by the compression mechanism is the portion corresponding with the cavity section, and is preferably at least 0.5 fold, and even more preferably at least 1 fold the maximum width of the cavity section, and is furthermore preferably no more than 30 fold, and even more preferably no more than 5 fold the maximum width of the cavity section. If the dimensions of the compression section are smaller than the above range, then the member becomes prone to breakage, whereas if the dimensions are larger than the above range, then the likelihood of interference with channels and other structures other than the targeted channel increases. The length of the compression region in the direction of the channel is preferably at least 0.5 fold, and even more preferably at least 1 fold the maximum width of the cavity section, in those cases in which the valve is designed to be either open or closed. In such cases, there is no need to place any particular restrictions on the upper limit for the length, although lengths of no more than 10 fold the maximum width of the cavity section enable easier opening and closing of the valve, and also reduce the variation in the volume of the valve section on opening and closing of the valve, and are consequently preferred. In those cases in which the valve is designed for flow rate regulation, the length is preferably at least 0.5 fold, and even more preferably at least 5 fold the maximum width of the cavity section.

There is no need to place any particular restrictions on the upper limit for the length, and in cases in which the channel itself forms the cavity section, the length may be the entire length of the channel. Increasing the length of the compression section makes regulation of the flow rate easier, and is consequently preferred. In either case, the compression region is preferably expanded as the thickness of the soft material (s) covering the cavity section is increased. The tip of the tip section of the compression mechanism may be rounded.

In those cases in which only the portion of the member corresponding with the cavity section, or the surrounding section is formed from the soft material (m), the compression region sits inside the portion formed from the soft material (s), and falls within the range described above.

In the first preferred embodiment of a micro chemical device of the present invention, a convex structure is preferably provided on the outer surface of the member formed from the soft material (s), in a position corresponding with the cavity section.

The maximum height of the convex structure is preferably at least 1 fold, and even more preferably at least 1.5 fold, and is furthermore preferably no more than 100 fold, and even more preferably no more than 10 fold the height of the cavity section. The maximum width of the convex structure is preferably at least 0.5 fold, and even more preferably at least 1 fold, and is furthermore preferably no more than 30 fold, and even more preferably no more than 5 fold the maximum width of the cavity section. The maximum length of the convex structure in the direction of the channel is preferably at least 0.5 fold, and even more preferably at least 1 fold the maximum width of the cavity section. There is no need to place any particular restrictions on the upper limit for the maximum length of the convex structure in the direction of the channel, although in those cases in which the valve is designed to be either open or closed, lengths of no more than 10 fold the maximum width of the cavity section enable easier opening and closing of the valve, and also reduce the variation in the volume of the valve section accompanying opening and closing of the valve, and are consequently preferred. In those cases in which the valve is designed for flow rate regulation, lengths of at least 5 fold the maximum width of the cavity section enable easier flow rate regulation. The dimensions of the convex structure preferably increase as the thickness of the soft material (s) covering the cavity section increases.

The material for the convex structure is arbitrary, and may utilize a soft material (s) or a hard material (h), although using a material with a higher tensile modulus of elasticity than the soft material (s) used as the material for forming the cavity section is preferred as it enables more reliable opening and closing, and flow rate control of the channel, and a hard material (h) with a tensile modulus of elasticity of at least 700 MPa is particularly preferred.

There are no particular restrictions on the method of manufacturing the convex structure, and in one suitable method, a cavity section is first formed between the member (A) and the member (B), and then a material for forming the convex structure is fixed to the outer surface in a position corresponding with the cavity section, using either bonding, caulking or lamination with another film. Alternatively, a member with a convex structure formed in advance as part of an integrated formed structure can also be used, or the convex structure can be formed at the same time as the formation of the members.

In cases such as the first preferred embodiment of the present invention, in which a convex structure is formed on the outside of the portion of the member formed from the soft material (s) in a position corresponding with the cavity section, the thickness of the portion corresponding with the cavity section and the height of the convex structure is calculated by considering the portion which is higher than the surrounding region to be the convex structure.

The shape of the convex structure is arbitrary, and possible shapes include a cylinder such as a circular cylinder or an angular cylinder, a pyramidal shape such as a cone or a pyramid, as well as trapezoidal, hemispherical or spherical shapes, although a hemispherical shape or a similar shape are preferred. By forming the compression mechanism as a convex structure, a number of effects are achieved in that (1) the opening and closing or flow rate regulation of only the single closest channel becomes easier to perform, (2) precise positioning of the mechanism which compresses the cavity section becomes unnecessary, and (3) the mechanism which pushes the convex structure can be formed as a flat surface, meaning the operation of the valve is easier and more reliable.

In those cases in which the first preferred embodiment of the present invention comprises a sheet type member (E) formed from a medium hard material (m) laminated to the outside of the portion corresponding with the cavity section formed from the soft material (s), a convex structure is preferably provided on the member (E) in a position corresponding with the cavity section, although this case is equivalent to a construction described below in which a sheet type member (H) with a convex structure is laminated, provided the tensile modulus of elasticity of the sheet type structure is a specified type of value.

Furthermore, a first preferred embodiment of the present invention also preferably comprises a member (H) provided with a convex structure at the portion corresponding with the cavity section, which is provided separately from the member (A) and the member (B), and this member (H) is positioned on the outer surface of the member formed from the soft material (s), in either a bonded or non-bonded state, with the convex structure facing the cavity section, and the relative positional relationship between the members is preferably fixed. The shape of the member (H) is arbitrary, although is preferably in the form of a sheet or a thin plate, and the member (H) is preferably laminated so as to cover the entire outer surface of the member formed from the soft material (s). The hardness of the member (H) is also arbitrary, although the member (H) is preferably formed from a medium hard material (m) or a hard material (h). When the sheet type structure is overlaid on the member with the cavity section, a deformable sheet or the like may also be sandwiched between the two layers.

The dimensions and shape of the convex structure are identical with the case described above in which a convex structure compression mechanism was formed on the outside of the portion corresponding with the cavity section formed from the soft material (s). The hardness and the thickness of the structure with the convex structure are arbitrary. Thick structures with high hardness levels are also possible.

By providing the member (H), the same effects can be achieved as the case described above in which a convex structure was formed on the outside of the portion corresponding with the cavity section formed from the soft material (s).

The member (H) may also be a sheet type member provided with a convex structure at the portion corresponding with the cavity section, which is provided separately from the member (A) and the member (B), and this sheet type member is preferably positioned on the outer surface of the member formed from the soft material (s), in either a bonded or non-bonded state, with the convex structure on the opposite side to the cavity section, and the relative positional relationship between the members is preferably fixed. This sheet type structure is preferably laminated so as to cover the entire outer surface of the member formed from the soft material (s). When the member (H) is overlaid on the member with the cavity section, a deformable sheet or the like may also be sandwiched between the two layers.

A sheet type member (H) in which the convex structure is fixed on the opposite side to the cavity section is formed from a material with a tensile modulus of elasticity within a range from 10 MPa to 10 GPa, and preferably from 100 MPa to 5 GPa. Furthermore, the thickness of the member is within a range from 0.5 μm to 500 μm, and preferably from 5 μm to 100 μm. A material with this type of tensile modulus of elasticity can be appropriately selected from amongst the materials listed as examples of the soft material (s) and the medium hard material (m).

Furthermore in such cases, the relationship between the tensile modulus of elasticity and the thickness of the sheet type member (H) must be within a range which displays flexibility of the sheet structure with respect to bending. The value of "tensile modulus of elasticity×thickness" is preferably within a range from $3\times10^{-4}$ to $1\times10^{-1}$ MPa·m, and even more preferably within a range from $3\times10^{-3}$ to $1\times10^{-2}$ MPa·m.

The material for the convex structure preferably has a tensile modulus of elasticity at least as large as the sheet type structure, but otherwise can be a similar material to that described above in the case in which a convex structure compression mechanism was formed on the outside of the portion corresponding with the cavity section formed from the soft material (s).

The dimensions and shape of the convex structure are identical with the case described above in which a convex structure was formed on the outside of the portion corresponding with the cavity section formed from the soft material (s).

By providing the member (H), the same effects can be achieved as both the case described above in which a convex structure compression mechanism was formed on the outside of the portion corresponding with the cavity section formed from the soft material (s), and the case in which a sheet type member (E) formed from a medium hard material (m) was laminated on the outside of the portion with the cavity section formed from the soft material (s).

The characteristics of a second preferred embodiment of the present invention are that (1) either the member (A) or the member (B) is formed from a soft material (s) at least within the portion which corresponds with the cavity section, (2) the other member to the member formed from the soft material (s) is formed from a medium hard material (m) at least within the region surrounding the cavity section, and the thickness of the portion of this member corresponding with the cavity section is within a range from 0.5 to 200 μm, and (3) the side from which compression of the cavity section by the compression mechanism occurs is the side of the member formed from the medium hard material (m), and with these exceptions, the embodiment is the same as the first preferred embodiment of the present invention. In other words, in the second preferred embodiment of the present invention, by compression of the cavity section via the member formed from the medium hard material (m), the member flexes with a larger curvature than the dimensions of the cavity section, and as a result the section surrounding the cavity section of the member formed from the soft material (s) undergoes deformation, causing a variation in the cross sectional area of the cavity section and thereby causing the device to function as a valve. The soft material (s), the medium hard material (m) and the hard material (h) are the same as those described for the first preferred embodiment.

The shape and thickness of the member formed from the soft material (s) are the same as for the first preferred embodiment of the present invention, with the exception that there are no restrictions on the thickness of the portion corresponding with the cavity section. However, the thickness of the portion corresponding with the cavity section is preferably no more than 10 mm, and even more preferably no more than 3 mm.

In those cases in which the member formed from the soft material (s) also comprises portions formed from a material other than the soft material (s), there are no restrictions on this material other than the soft material (s), and this requirement is also identical with the case of the first preferred embodiment.

The member formed from the soft material (s) is preferably formed on top of a base material. The base material is preferably formed from a medium hard material (m) or a hard material (h). In cases in which the member formed from the soft material (s) has no base material, or in cases in which the material used for the base material has a tensile modulus of elasticity of less than 700 MPa, then either compression must be performed using the compression mechanism described below positioned on top of a hard base, or alternatively a compression mechanism must be used which sandwiches the portion to be compressed from both the member (A) side and the member (B) side. However, if the member formed from the soft material (s) is formed using either a medium hard material (m) or a hard material (h), then these restrictions disappear, and there is an increase in the potential places in which the micro chemical device of the present invention can be used.

If the member formed from the medium hard material (m) utilizes a material with an even higher tensile modulus of elasticity, then restricting the flow rate or completely closing the valve becomes difficult, and the opening and closing of only one of a plurality of adjacent valve mechanisms also becomes difficult. A suitable tensile modulus of elasticity range depends on factors such as the shape of the cavity section, and the thickness of the portion of the member (B) formed from the medium hard material (m), and as the height of the cavity section reduces and the thickness of the above portion becomes thinner, a material with a comparatively higher tensile modulus of elasticity can be used.

The member formed from the medium hard material (m) may also be formed using another material in the sections outside the portion corresponding with the cavity section. In such cases, the material for the sections outside the portion corresponding with the cavity section is preferably a material with a tensile modulus of elasticity exceeding 10 GPa. By using this type of material, the pressure resistance of the micro chemical device of the present invention can be increased.

In the second preferred embodiment of the present invention, by compressing the outer surface of the member formed from the medium hard material (m), the member flexes, causing a deformation of the member formed from the soft material (s), thereby altering the space within the cavity section, and causing the device to function as a valve. Accordingly, as the value of the tensile modulus of elasticity of the member formed from the medium hard material (m) increases, and the thickness of the member increases, the area of the portion formed from the medium hard material (m) must be expanded. Forming the member formed from the medium hard material (m) entirely from the medium hard material (m) offers greater ease of production, and is consequently preferred.

The thickness of the portion of the member formed from the medium hard material (m) which corresponds with the cavity section [hereafter described as the "thickness of the member formed from the medium hard material (m)"] is within a range from 0.5 µm to 200 µm, and preferably from 5 µm to 100 µm, and even more preferably from 5 µm to 50 µm. The member (B) is preferably a sheet of uniform thickness.

If the thickness of the member is overly thin, then rupture of the member formed from the medium hard material (m) becomes more likely, whereas in contrast if the member is overly thick, then complete closure of the valve becomes difficult, and the opening and closing of only one of a plurality of adjacent valve mechanisms also becomes difficult.

As the tensile modulus of elasticity of the material used increases, the thickness of the member formed from the medium hard material (m) is preferably reduced. The relationship between the tensile modulus of elasticity and the thickness of the member (B) yields a value of "tensile modulus of elasticity×thickness" which is preferably within a range from $3\times10^{-4}$ to $1\times10^{-1}$ MPa·m, and even more preferably within a range from $3\times10^{-3}$ to $1\times10^{-2}$ MPa·m.

By using this type of medium hard material (m) for the material on the side subject to compression, and setting the thickness to a value within the above range, the opening and closing of only one of a plurality of adjacent valve mechanisms becomes possible, the pressure resistance also improves, the breaking strength of that portion increases, and the thickness of, the micro chemical device can be reduced.

The case in which the member formed from the medium hard material (m) is the member (B) enables easier control of the thickness of the outer member, and is consequently preferred.

The method for bonding the member (A) and the member (B) can be the same as the method used in the first preferred embodiment of the present invention.

The use of a compression mechanism, a convex structure and a member (H) in the second preferred embodiment of the present invention are the same as the cases described for the first preferred embodiment of the present invention. However, whereas in the first embodiment the cavity section was compressed from the side of the member formed from the soft material, in the second embodiment, the compression is performed from the side of the member (B) formed from the medium hard material (m). In addition, in those cases in which a convex structure is formed on top of the member formed from the medium hard material (m), the thickness of the portion corresponding with the cavity section is taken as the thickness excluding the convex structure.

Another type of micro chemical device of the present invention is a micro chemical device with a valve function, in which by bonding a member (B) and a member (C) together, with a layer type member (D) comprising a lacking section for forming a channel disposed therebetween, a capillary type channel is formed between the member (B) and the member (C) by the lacking section of the material of the member (D), and a cavity section is formed partway along the channel, and one of the members (B), (C) and (D)

is formed from a soft material (s), at least within the portion which corresponds with the cavity section (or in the case of the member (D), the portion surrounding the cavity section), and one of the members (B), (C) and (D) is formed from either a medium hard material (m) or a hard material (h), at least within the portion which corresponds with the cavity section (or in the case of the member (D), the portion surrounding the cavity section), wherein the cavity section is compressed from the side of the member (B), and the volume of the cavity section can be reduced in a reversible manner.

In a micro chemical device of the present invention formed from the members (B), (C) and (D), the member (B) is preferably formed from a soft material (s), at least within the portion which corresponds with the cavity section (or in the case of the member (D), the portion surrounding the cavity section), and the minimum value of the thickness of the portion corresponding with the cavity section is preferably within a range from 10 to 3000 µm. Alternatively, the member (B) is formed from a medium hard material (m), at least within the portion which corresponds with the cavity section, and the minimum value of the thickness of the portion corresponding with the cavity section is preferably within a range from 0.5 to 500 µm.

In a micro chemical device of the present invention formed from the members (B), (C) and (D), when the member (C) is positioned on the lower side and the member (B) is positioned on top (hereafter in this type of micro chemical device, and in a third, fourth and fifth embodiment, the terms "up", "down" and "height" are used to describe this situation), then the bottom surface of the channel is formed by the member (C), the side surfaces are formed by the member (D), and the upper surface is formed by the member (B). The dimensions and shape of the channel are the same as described for the first preferred embodiment of the present invention.

The cavity section is formed in a similar manner to the channel, by sandwiching the lacking section of the member (D) between the member (C) and the member (B). The position, the dimensions and the shape of the cavity section are the same as described for a micro chemical device formed from a member (A) and a member (B) of the present invention.

There are no particular restrictions on the external shape of the member (C), and with the exception that a groove need not be provided in the surface, the same shapes as those described for the member (A) in a micro chemical device formed from a member (A) and a member (B) can be used. The member (C) need not have a groove formed in the surface, but may also comprise a groove or other structures. For example, the member (C) may have a groove, and that groove may connect with the lacking section of the member (D) forming a connected channel.

The member (C) may comprise portions formed from a plurality of materials when viewed from a direction perpendicular to the member surface, or may comprise a plurality of layers when viewed from a side direction.

With the exception of the fact that the member (B) is laminated and bonded to the member (D) and not the member (A), the device is the same as the micro chemical device of the present invention formed from a member (A) and a member (B), with the term "member A" replaced with the term "a layered structure of a member (C) and a member (D)". The member (B) need not have a groove formed in the surface, but may also comprise a groove or other structures. For example, the member (B) may have a groove, and that groove may connect with the lacking section of the member (D) forming a connected channel.

The member (D) is a layer type member, and the thickness of the member may be equal to the height of the channel of the present invention. The lacking section formed in the member (D) penetrates from the upper surface through to the lower surface of the member (D), and when sandwiched between the member (C) and the member (B), the lacking section forms the channel and the cavity section. The shape of the lacking section can be formed in the shape of the desired channel and cavity section. Accordingly, provided the member (D) is of a shape that can be sandwiched between the member (C) and the member (B) in a fluid tight manner, the thickness of the member (D) need not necessarily be uniform.

The structure and the dimensions of the channel and the cavity section are the same as described for the micro chemical device of the present invention formed from a member (A) and a member (B), with the exception that instead of being formed by a groove in the member (A) and the member (B), the channel and the cavity section are formed by sandwiching the lacking section of the member (D) between the member (C) and the member (B).

There are no particular restrictions on the method of providing the lacking section, which forms the channel, in the member (D), and suitable methods include photolithography (including radiation lithography), etching methods, vapor deposition methods, vapor phase polymerization methods, cutting methods, and methods in which a position opened between a plurality of sheet type members is cured in the presence of a protective material. The lacking section can also be formed at the same time that the member (D) is formed between the member (C) and the member (B). Structures other than the channel and the cavity section, such as structures or lacking sections which function as fluid storage vessels, reaction vessels, or analysis mechanisms, may also be provided in the member (D). The operation of forming a lacking section is preferably performed on top of a base material, with the base material then removed at the final stage.

There are no particular restrictions on the method for sandwiching and bonding the member (D) with the lacking section for forming the channel between the member (C) and the member (B). Suitable methods which can be employed include (1) a method in which an uncured coating layer of a radiation-curable composition is formed on top of the member (C), the entire layer except for the portion to become the lacking section is irradiated with an activating radiation to semi cure the irradiated portion, the non-irradiated uncured portion of the composition is removed and the member (B) is then positioned on top of the semi cured layer, and the structure is then irradiated a second time with an activating radiation to cure and bond the member (D) layer, (2) a method in which an uncured coating layer of a radiation-curable composition is formed on top of the member (C), the entire layer except for the portion to become the lacking section is irradiated with an activating radiation to cure the irradiated portion, the non-irradiated uncured portion of the composition is removed to form the lacking section of the member (D), the member (B) which is formed from a semi cured product of a radiation-curable composition is then positioned on top of the member (D), and the structure is then irradiated a second time with an activating radiation to cure and bond the member (B), (3) a method in which a radiation-curable composition is sandwiched between the member (C) and the member (B), the entire layer of the composition except for the portion to become the channel is irradiated with an activating radiation from outside the member (C) and/or the member (B), and the uncured portion of the radiation-curable composition is then removed to form the channel, (4) a method in which an adhesive sheet type member (D), with the portion to become the channel cut out and removed, is sandwiched between and bonded to the member (C) and the member (B), (5) a method in which a protective material such as a rod of tetrafluoroethylene is placed between the member (C) and the member (B) in a position which is to become the channel, and following the filling of the gap between the members with a heat curing or radiation-curable resin or molten resin and subsequent curing, the protective material is removed, and (6) a method in which independently formed members are bonded together using a solvent based adhesive (such as a radiation-curable composition), using a solvent free adhesive, using a molten adhesive, by applying a solvent to the surface of the members, or using fusion achieved by either heat or ultrasound.

The region which compresses the member via the compression mechanism, and the compression mechanism itself are the same as described for the micro chemical device of the present invention formed from the members (A) and (B). Compression may be performed from the side of the member formed from a soft material (s) of specified thickness, and can also be performed from the side of the member formed from a medium hard material (m) of specified thickness. This functionality is also as described above.

The use of a convex structure or a member (H) with a convex structure is also as described above.

As follows is a description of preferred embodiments (a third, fourth and fifth embodiment) of a micro chemical device of the present invention formed from members (B), (C) and (D).

In a third preferred embodiment, the member (B) is formed from a soft material (s) with a tensile modulus of elasticity within a range from 1 to 700 MPa, and preferably from 1 to 400 MPa, at least within the portion which corresponds with the cavity section. If the tensile modulus of elasticity value exceeds the above range then regulation of the flow rate becomes difficult, and the device is more prone to breakage at the valve portion.

The thickness of the portion of the member (B) which corresponds with the cavity section [hereafter, this thickness may be described as the "thickness of the member (B)"] is the same as that described for the member on the side subject to compression formed from the soft material (s) in the first preferred embodiment of the present invention.

Sections of the member (B) outside the portion corresponding with the cavity section may be formed from other materials, or the entire member (B) may be formed from the soft material (s). Devices in which the member (B) is a sheet type member formed entirely from a soft material (s) more readily exhibit the effects of the present invention, and are also easier to manufacture, and are consequently preferred.

The portion of the member (B) corresponding with the cavity section is also preferably a layered product formed from a plurality of materials with different tensile modulus of elasticity values, each of which has a tensile modulus of elasticity consistent with a soft material (s). This requirement is the same as that described for the member on the side subject to compression formed from the soft material (s) in the first preferred embodiment of the present invention.

A member (E) formed from a medium hard material (m) with a tensile modulus of elasticity within a range from 700 MPa to 10 GPa, and preferably from 1 GPa to 5 GPa, is preferably laminated to the outside of the portion of the member (B) corresponding with the cavity section. This requirement is also the same as that described in the first preferred embodiment of the present invention, for the lamination of a member (E) to the outside of the member on the side subject to compression formed from the soft material (s).

In the third preferred embodiment of the present invention, the material for the member (D) is arbitrary. In other words, the material may be a soft material (s), a medium hard material (m) or a hard material (h). However, in terms of making it easier to achieve complete closure of the channel, the member (D) is preferably formed from a soft material (s).

In the third preferred embodiment of the present invention, the member (C) is formed from either a medium hard material (m) or a hard material (h) at least within the portion surrounding the cavity section.

There are no particular restrictions on the thickness of the member (C), in a similar manner to the base material in the first preferred embodiment of the present invention, on which was formed the member formed from the soft material (s).

Sections of the member (C) outside the portion surrounding the cavity section may be formed from other materials, or the entire member (B) may be formed from the same material. Devices in which the member (B) is a sheet type member formed entirely from the same material more readily exhibit the effects of the present invention, and are also easier to manufacture, and are consequently preferred.

In the third preferred embodiment of the present invention, the valve function is activated by selectively compressing the cavity section from the side of the member (B) formed from the soft material (s). The use of compression mechanisms, convex structures and a member (H) in this embodiment are the same as described for the first preferred embodiment of the present invention.

A fourth preferred embodiment of the present invention is a modified structure of the third preferred embodiment of the present invention comprising the member (C), the member (B) and the member (D) as structural elements, wherein the member (B) is formed from a medium hard material (m), the member (C) is formed from a soft material (s), and the cavity section is compressed from the side of the member (B).

The external shape of the member (C) in the fourth preferred embodiment of the present invention is the same as that described for the third preferred embodiment of the present invention. The member (C) is formed from a soft material (s) at least within the portion which corresponds with the cavity section. If the tensile modulus of elasticity value exceeds this value then regulation of the flow rate becomes difficult, and the device is more prone to breakage at the valve portion. The thickness of the portion of the member (C) which corresponds with the cavity section is the same as the thickness of the portion corresponding with the cavity section in the member formed from the soft material (s) in the second preferred embodiment of the present invention.

Sections of the member (C) outside the portion corresponding with the cavity section may be formed from other materials, or the entire member (C) may be formed from the soft material (s). Devices in which the member (C) is a sheet type member formed entirely from a soft material (s) more readily exhibit the effects of the present invention, and are also easier to manufacture, and are consequently preferred. The member (C) is preferably formed on top of a hard base material. The base material may be the same as the base material described in the second preferred embodiment of the present invention.

The member (B) in the fourth preferred embodiment of the present invention is the same as the member formed from a medium hard material (m) in the second preferred embodiment of the present invention, with the exception that instead of being bonded to the member (A), the member (B) is bonded to a layered product of the members (C) and (D).

The shape and the material of the member (D) in the fourth preferred embodiment of the present invention, and the lacking section provided in the member (D) are the same as for the member (D) in the third preferred embodiment of the present invention.

Similarly, the method of sandwiching and bonding the member (D) with a lacking section for forming the channel between the member (C) and the member (B) is the same as that described in the third preferred embodiment of the present invention.

The region which compresses the member via the compression mechanism, and the compression mechanism itself are the same as described for the second preferred embodiment of the present invention. Furthermore, the use of a compression mechanism, a convex structure or a member (H) are the same as the cases described in the second preferred embodiment of the present invention.

A fifth preferred embodiment of the present invention is a modified structure of the third preferred embodiment of the present invention comprising the member (C), the member (B) and the member (D) as structural elements, wherein the member (D) is formed from a soft material, the member (B) is formed from a medium hard material (m), and the member (C) is formed from either a medium hard material (m) or a hard material (h), and by applying compression from the side of the member (B), mainly the member (D) undergoes deformation, causing a variation in the spatial dimensions of the cavity section and thereby enabling opening and closing of the channel or regulation of the flow rate.

In other words, the device is the same as that of the third preferred embodiment of the present invention with the exceptions that the member (B) is formed from a medium hard material (m) at least within the portion which corresponds with the cavity section, the thickness of the portion of the member (B) which undergoes compression is within a range from 0.5 to 200 µm, the member (D) is formed from a soft material (s) at least within the portion which corresponds with a the cavity section, and the fact that a compression mechanism is provided for compressing the cavity section via the member (B).

The shape, structure and dimensions of the member (C) in the fifth preferred embodiment of the present invention are the same as described in the third preferred embodiment of the present invention. In other words, the member (C) may be formed from either a medium hard material (m) or a hard material (h), although members formed from a hard material (h) are preferred.

In the fifth preferred embodiment of the present invention, there are no particular restrictions on the shape, structure or surface form of the member (B) provided a capillary type channel and a cavity section can be formed using the member (C), the member (B) and the lacking section of the member (D), by bonding the member (D) in a position sandwiched between the member (B) and the member (C). These requirements are the same as those described for the member (B) in the second preferred embodiment of the present invention.

In the fifth preferred embodiment of the present invention, the member (B) is formed from a medium hard material (m) at least within the portion which corresponds with the cavity section. Devices in which the member (B) is a sheet type member formed entirely from the same material more readily exhibit the effects of the present invention, and are also easier to manufacture, and are consequently preferred. This requirement is the same as the member (B) in the second preferred embodiment of the present invention. The thickness of the member (B) is also the same as that described in the second preferred embodiment of the present invention.

In the fifth preferred embodiment of the present invention, the member (D) is formed form a soft material (s) at least in the portion surrounding the cavity section, namely the portion surrounding the walls of the cavity section. If the tensile modulus of elasticity value falls outside the above range then regulation of the flow rate becomes difficult, and the device is more prone to breakage at the valve portion.

In the fifth preferred embodiment of the present invention, the cavity section is selectively compressed from the side of the member (B) formed from the medium hard material (m). The region which compresses the member via the compression mechanism, and the compression mechanism itself are the same as described for the second preferred embodiment of the present invention. Furthermore, the use of a compression mechanism, a convex structure or a member (H) are the same as the cases described in the second preferred embodiment of the present invention.

Another micro chemical device of the present invention comprises an aforementioned member (A) and a member (B), and both of these members are formed from a soft material (s), and either an aforementioned convex structure or a member (H) is provided thereon. With the exception that both the member (A) and the member (B) are formed from a soft material (s), the structure, members, manufacturing method, and usage method and the like of this type of micro chemical device are the same as for the micro chemical device described above, comprising a member (A) and a member (B) in which one of these two members was formed from a soft material (s). Furthermore, the use of a convex structure or a member (H) are also the same as the cases described above in which the convex structure or a member (H) was formed on, or fixed to, a member formed from a soft material (s).

Yet another micro chemical device of the present invention comprises members (B), (C) and (D), and all of these members are formed from a soft material (s), and either an aforementioned convex structure or a member (H) is provided thereon. With the exception that all of the members (B), (C) and (D) are formed from a soft material (s), the structure, members, manufacturing method, and usage method and the like of this type of micro chemical device are the same as for the micro chemical device of the present invention described above, comprising members (B), (C) and (D), in which one of these members was formed from a soft material (s), and one of the members is formed from either a medium hard material (m) or a hard material (h). Furthermore, the use of a convex structure or a member (H) are also the same as the cases described above in which the convex structure or a member (H) was formed on, or fixed to, a member formed from a soft material (s).

EXAMPLES

As follows is a more detailed description of the present invention using a series of examples and comparative examples, although the present invention is in no way restricted to the examples presented. In the following examples, unless otherwise stated, the units "parts" refer to "parts by weight"

<Measurement of Tensile Modulus of Elasticity and Breaking Elongation>

[Measurement Samples]

Flat plate or sheet type samples were cut into strip samples of width 10 mm and length 100 mm. Radiation-curable composition cured product samples were produced by applying a radiation-curable composition to a glass plate, curing the composition under a stream of nitrogen by irradiation for 30 seconds with an ultraviolet beam of strength 50 mW/cm$^2$ at 365 nm, and then removing the cured product from the glass plate and cutting the product into strip samples of width 10 mm and length 100 mm.

These samples were left to stand for at least 16 hours at 24±1° C. and 55±5% humidity, before being subjected to measurement.

[Measurement]

A "Strograph V1-C" manufactured by Toyo Seiki Seisaku-sho, Ltd was used, and measurements were conducted in an atmosphere of 24±1° C. and 55±5% humidity, using a distance between clamp heads of 80 mm and a cross-head speed of 20 mm/minute.

<Materials>

As follows is a description of the materials used in the examples and their abbreviations.

[Radiation-curable Compounds]

(1) A trifunctional urethane acrylate oligomer (Unidic V4263, manufactured by Dainippon Ink and Chemicals, Inc.); abbreviation "Unidic V4263"

(2) A diacrylate mixture comprising ω-tetradecanediol diacrylate and ω-pentadecanediol diacrylate as main constituents (Sartomer C2000, manufactured by Somar Corporation); abbreviation "Sartomer C2000"

(3) Tetramethylene glycol (average molecular weight 650) maleimide acetate (synthesized using the method disclosed in synthetic example 18 of Japanese Unexamined Patent Application, First Publication No. Hei 11-124403); abbreviation "TGMA"

(4) Dicyclopentanyl diacrylate ("R-684", manufactured by Nippon Kayaku Co., Ltd.); abbreviation "R-684"

[Amphipathic Polymerizable Compound]

(5) Nonylphenoxypolyethylene glycol (n=17) acrylate ("N-177E", manufactured by Dai-ichi Kogyo Seiyaku Co., Ltd.; HLB value=14.64; soluble in both water and a mixed solvent of cyclohexane/toluene); abbreviation "N-177E"

[Ultraviolet Polymerization Initiator]

(6) 1-hydroxycyclohexylphenylketone (Irgacure 184, manufactured by Ciba Geigy Corporation); abbreviation "Irgacure 184"

[Polymerization Retarding Agent]

(7) 2,4-diphenyl-4-methyl-1-pentene (manufactured by Kanto Kagaku Co., Ltd.); abbreviation "DPMP"

[Thermoplastic Polymers and Formed Products Thereof]

(8) Polystyrene ("Dicstyrene XC-520", manufactured by Dainippon Ink and Chemicals, Inc.); abbreviation "polystyrene [m1]"

(9) Polypropylene biaxially stretched sheet ("FOR", manufactured by Futamura Chemical Industries Co., Ltd., thickness 30 μm, one surface corona treated); abbreviation "OPP sheet"

(10) Syndiotactic polystyrene biaxially stretched sheet (manufactured by Idemitsu Petrochemical Co., Ltd., thickness approximately 10 μm); abbreviation "OSPS sheet [m2]"

(11) Acrylic resin ("Delpet 670N", manufactured by Asahi Kasei Corporation); abbreviation "[m3]"

(12) Polystyrene biaxially stretched sheet (prototype manufactured by Dainippon Ink and Chemicals, Inc., thickness 60 μm); abbreviation "OPS sheet [m4]"

(13) Polyurethane ("Elastollan F564", manufactured by Nippon Elastollan Industries Ltd.); abbreviation "[s1]"

(14) Polyurethane ("Elastollan F580", manufactured by Nippon Elastollan Industries Ltd.); abbreviation "[s2]"

(15) Soft polyvinyl chloride ("Z-4370", manufactured by Denki Kagaku Kogyo Kabushiki Kaisha); abbreviation "PVC [s3]"

(16) Ethylene-vinyl acetate copolymer resin ("Sholex EVA, BF05-6", manufactured by Showa Denko K.K.); abbreviation "EVA [s4]"

(17) Polyamide elastomer ("Grilux A-100", manufactured by Dainippon Ink and Chemicals, Inc.); abbreviation "polyamide elastomer [s5]"

(18) Polyester elastomer ("Grilux E-120", manufactured by Dainippon Ink and Chemicals, Inc.); abbreviation "polyester elastomer [s6]"

(19) Modified polyolefin ("N polymer R4100", manufactured by Nippon Oil Corporation); abbreviation "modified polyolefin [s7]"

<Preparation of Radiation-curable Compositions>

The methods of preparing the radiation-curable compositions used in the examples are shown below.

[Preparation of a Radiation-curable Composition [e1]]

40 parts of Unidic V4263, 60 parts of Sartomer C2000, 5 parts of Irgacure 184 as an ultraviolet polymerization initiator, and 0.1 parts of DPMP as a polymerization retarding agent were mixed together, yielding a radiation-curable composition [e1].

[Preparation of a Radiation-curable Composition [e2]]

20 parts of Unidic V4263, 80 parts of Sartomer C2000, 5 parts of Irgacure 184, and 0.1 parts of DPMP were mixed together, yielding a radiation-curable composition [e2].

[Preparation of a Radiation-curable Composition [e3]]

50 parts of TGMA, and 50 parts of Sartomer C2000 were mixed together, yielding a radiation-curable composition [e3].

[Preparation of a Radiation-curable Composition [e4]]

100 parts of Unidic V4263, 5 parts of Irgacure 184, and 0.1 parts of DPMP were mixed together, yielding a radiation-curable composition [e4].

[Preparation of a Radiation-curable Composition [e5]]

10 parts of Unidic V4263, 90 parts of R-684, and 5 parts of Irgacure 184 were mixed together, yielding a radiation-curable composition [e5].

[Preparation of a Radiation-curable Composition [e6]]

80 parts of Unidic V4263, 20 parts of N-177E as an amphipathic polymerizable compound, 0.1 parts of DPMP as a polymerization retarding agent, and 5 parts of Irgacure 184 as a photopolymerization initiator were mixed uniformly together, yielding a composition [e6].

[Preparation of a Radiation-curable Composition [e7]]

10 parts of Unidic V4263, 70 parts of R-684, 20 parts of N-177E, 0.1 parts of DPMP, and 5 parts of Irgacure 184 were mixed together, yielding a radiation-curable composition [e7].

[Preparation of a Radiation-curable Composition [e8]]

20 parts of Unidic V4263, 60 parts of Sartomer C2000, 20 parts of N-177E, 0.1 parts of DPMP, and 5 parts of Irgacure 184 were mixed together, yielding a radiation-curable composition [e8].

Example 1

This example presents an example of the first embodiment of the present invention.

[Preparation of a Member (A)]

Figure 1B:
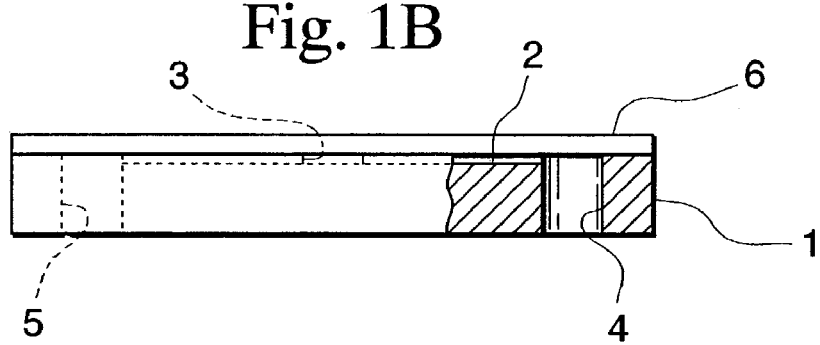

A flat plate type substrate (1) of dimensions 2.5 cm×5 cm×thickness 3 mm formed from polystyrene [m1] was heated with an electric hot air torch to soften the surface, subsequently pressed onto a glass template (not shown in the drawings) heated to a temperature of 180° C. and then cooled, and subsequently peeled off the template, thereby forming in the surface of the substrate (1), a groove (2) of width 30 µm, depth 30 µm and length 30 mm with a substantially rectangular cross section, and a circular cylindrical concave section (3) of diameter 90 µm and depth 30 µm formed partway along the groove, and furthermore an inlet (4) and an outlet (5) were formed at both ends of the groove (2) by opening drill holes of diameter 0.5 mm, thereby completing the preparation of a member (A) (hereafter referred to as [A1]) of the form shown in FIG. 1.

[Bonding of a Member (B)]

The radiation-curable composition [e1] was applied to the corona treated surface of an OPP sheet (not shown in the drawings) using a 127 µm bar coater, and subsequently subjected to a 1 second irradiation of ultraviolet light of strength 50 mW/cm$^2$ in a nitrogen atmosphere using a multilight 200 type light source unit manufactured by Ushio Inc., forming an incompletely cured coating with no fluidity, and the surface of this coating was bonded to the surface of the member [A1] in which the groove had been formed. Subsequently, by subjecting the coating to a further 30 seconds of irradiation with the same ultraviolet light from the OPP sheet side of the structure to complete the curing of the coating, a sheet type member (B) (hereafter referred to as [B1]) (6) of thickness 64 µm formed from a soft material (s) comprising a cured product of the radiation-curable composition [e1] was formed and bonded to the surface of the member [A1], thereby forming a capillary type channel (2) and a cavity section (3) formed partway along the channel between the two members. Subsequently, the OPP sheet was peeled away, yielding a micro chemical device [#1] of the form shown in FIG. 1.

[Tensile Characteristics of the Member (B)]

In a separate preparation, a cured sheet of the radiation-curable composition [e1] was prepared, and the tensile characteristics were measured. The results are shown in Table 1. Table 1 also shows the tensile characteristics of the polystyrene [m1] used. From Table 1 it is clear that the cured radiation-curable composition [e1] is a soft material (s), whereas the polystyrene [m1] is a medium hard material (m).

[Preparation of a Compression Mechanism]

Figure 2:
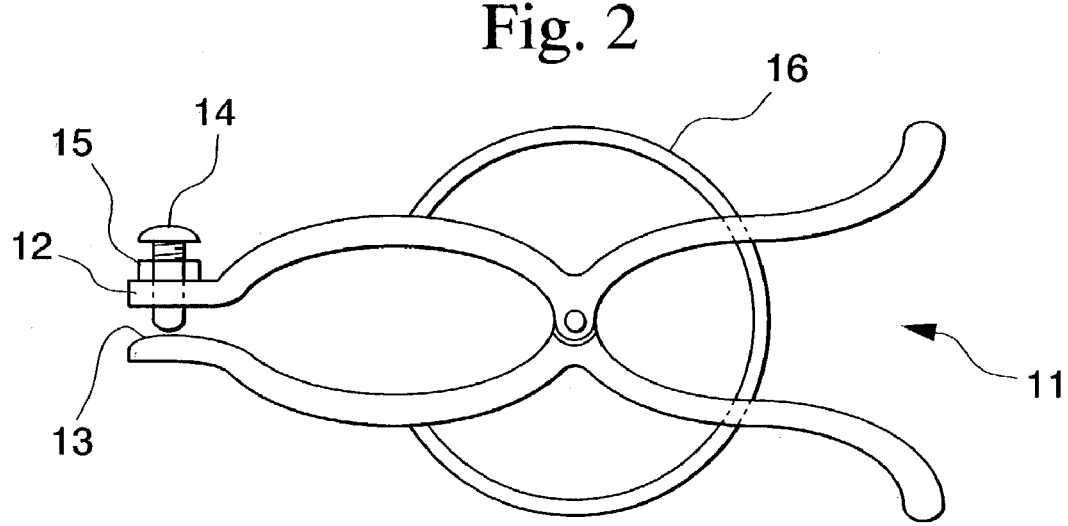
FIG. 2 is a sketch of a clamp type compression mechanism used in the example 1.

A spring type clamp (11) such as that shown in FIG. 2 was prepared, comprising an 8 mm×8 mm flat plate type upper clamp section (12) and a gently curved lower clamp section (13), and an M2 screw hole was formed in the center of the upper clamp section (12), and an M2 screw (14) cut to a conical shape with the tip rounded off to a hemispherical shape of radius 0.25 mm was screwed into the screw hole and fixed by a lock nut (15) in a position wherein the tip of the screw protruded from the flat surface of the upper clamp by 0.2 mm forming a protruding section.

[Channel Opening and Closing Test]

When water colored with methylene blue (manufactured by Wako Pure Chemical Industries, Ltd.) was injected into the capillary tube via the inlet (4) using a microsyringe, the water exited from the outlet (5). Next, using the spring type clamp prepared above, the cavity section (3) of the micro chemical device [#1] was compressed from the side of the member (B) using the protruding section of the clamp, and the water flow was interrupted without rupturing the member (B), and when the clamp was released the channel was reopened. At this time, no breakage of the member (B) was observed. The test was repeated 10 times, and the same effects were observed on each occasion.

Example 2

This example presents an example of the first embodiment of the present invention in which a screw type compression mechanism is fixed to the device.

[Preparation of a Micro Chemical Device Precursor]

A micro chemical device [#1] prepared in exactly the same manner as the example 1 was used as the precursor for a micro chemical device [#2]

[Preparation and Fixing of a Compression Mechanism]

Using a plate formed from the same polystyrene [m1] as that used for the member [A1], a compression mechanism substrate of the same dimensions as the member [A1] was prepared, a screw hole was formed in a position corresponding with the cavity section (3), a screw cut to a conical shape with the tip rounded off to a hemispherical shape of radius 0.25 mm was mounted in the screw hole to form a member [H2], and by applying the radiation-curable composition [e4] to the section surrounding the member [H2] to a width of approximately 5 mm, and then bonding the member onto the member [B1] using ultraviolet radiation, a micro chemical device [#2] with the member [H2] fixed in a position corresponding with the cavity section was prepared.

[Channel Opening and Closing Test]

When water colored with methylene blue (manufactured by Wako Pure Chemical Industries, Ltd.) was injected into the inlet (4) at a constant pressure using a microsyringe, the water exited from the outlet (5) at a constant flow rate. By compressing the cavity section (3) from above the member [B1] by gradually closing the screw of the micro chemical device, the flow rate could be varied in accordance with the degree to which the screw had been closed.

Example 3

This example presents an example of the first embodiment of the present invention in which a convex structure is provided on the surface of a member formed from a soft material (s) at a portion corresponding with the cavity section.

[Preparation of a Micro Chemical Device]

A small drop of the radiation-curable composition [e4] was placed on the surface of the member [B1] of a micro chemical device [#1] obtained in the example 1, in a position corresponding with the cavity section, and subsequently cured by irradiation with ultraviolet light, thereby yielding a micro chemical device [#3] with a convex structure of diameter 0.6 mm and height 0.22 mm.

[Preparation of a Compression Mechanism Actuation Mechanism]

A spring type clamp of the same construction as the compression mechanism produced in the example 1, but with the exception that the screw (14), the lock nut (15) and the screw hole were not provided, was prepared as a mechanism for actuation of the convex structure compression mechanism, and subsequently used as an actuation mechanism. Furthermore, a brass rod with a flat tip of diameter 6 mm was also prepared as another actuation mechanism.

[Channel Opening and Closing Test]

Using the clamp type actuation mechanism prepared above, by compressing the region comprising the convex structure of the micro chemical device using the upper clamp section (12), the water flow was interrupted, and when the clamp was released, the channel was reopened. Unlike the example 1, in this example the opening and closing of the channel could be achieved reliably even without having to accurately position the protruding section of the compression mechanism.

Furthermore, using the rod like actuation mechanism prepared above and compressing the region comprising the convex structure manually, the same effects were achieved.

Example 4

This example presents an example of the first embodiment of the present invention in which a convex structure compression mechanism formed from a medium hard material (m) is provided on the surface of the member subjected to compression.

[Preparation of a Micro Chemical Device]

With the exception of using the radiation-curable composition [e5] for forming the convex structure, preparation was conducted in a similar manner to the example 3, yielding a micro chemical device [#4] with a convex structure compression mechanism of hemispherical shape with a diameter of approximately 230 μm formed from a medium hard material (m).

[Channel Opening and Closing Test]

Tests were conducted in the same manner as the example 3, and the same effects as the example 3 were achieved.

Example 5

This example presents an example of the first embodiment of the present invention in-which the compression mechanism is a sheet type member (H) with a convex structure provided on the surface, and this mechanism is fixed to the surface of the micro chemical device with the convex structure facing inwards.

[Preparation of a Micro Chemical Device]

A micro chemical device [#5] was prepared in the same manner as the example 2, with the exceptions that a member [H5] with a convex structure formed thereon was prepared by bonding a glass sphere (52) with a diameter of approximately 0.5 mm onto the surface of a sheet type member (51) formed from an OSPS sheet [m2] using the radiation-curable composition [e4] as an adhesive (53), and this member was then positioned in a position corresponding with the cavity section (3) with the convex structure facing the cavity section, instead of the screw type compression mechanism used in the example 2, and the four corners of the member were bonded to the member (B) using the radiation-curable composition [e4] as an adhesive (54), thereby fixing the member to the member (B).

[Channel Opening and Closing Test]

Tests were conducted in the same manner as the example 3, and the same effects as the example 3 were achieved.

Example 6

This example presents an example of the first embodiment of the present invention in which the compression mechanism is a sheet type member (H) with a convex structure provided on the surface, and this member (H) is fixed to the device with the convex structure facing outwards.

[Preparation of a Micro Chemical Device]

A micro chemical device [#6] was prepared in the same manner as the example 4, with the exception that the sheet type member [H5] with a convex structure prepared in the example 5 was fixed to the device with the convex structure positioned on the opposite side to the cavity section.

[Channel Opening and Closing Test]

Tests were conducted in the same manner as the example 3, and the same effects as the example 3 were achieved.

Comparative Example 1

Using a micro chemical device provided with neither a convex structure compression mechanism nor a sheet type member (H) with a convex structure provided on the surface thereof, namely, using a micro chemical device [#1] instead of the micro chemical devices [#3], [#4], [#5] and [#6], channel opening and closing tests were conducted in the same manner as the examples 3, 4, 5 and 6, but the flow of water was not interrupted.

Example 7

This example presents an example of the first embodiment of the present invention in which the member (B) is a sheet type member formed from 2 layers of a soft material (s).

[Preparation of a Micro Chemical Device]

A micro chemical device [#7] in which the member (B) is a sheet type member formed from 2 layers of a soft material (s) was prepared in the same manner as the example 2, with the exceptions that (1) the radiation-curable composition [e2] was used instead of the radiation-curable composition [e1], (2) a hot pressed sheet of thickness 500 μm formed from a soft material (s) of polyurethane [s1] was used instead of the OPP sheet, and (3) after formation of the member (B), the sheet was not peeled off, but was rather used as the micro chemical device in a laminated and bonded state.

The tensile characteristics of cured products formed from the sheet of polyurethane [s1] and the radiation-curable composition [e2] are shown in Table 1.

[Flow Rate Regulation Test]

When tests were conducted in the same manner as the example 2, the same effects as the example 2 were achieved. In addition, even if the screw was closed so tightly that in the case of the single layer member (B) formed from a cured product of the radiation-curable composition [e2], a hole opened in the portion compressed by the screw and fluid leakage occurred, in the present example, no such leakage occurred. Furthermore, even if opening and closing repetitions were completed until the point that in the case of the single layer member (B) formed from a cured product of the radiation-curable composition [e2], a hole opened in the portion compressed by the screw and fluid leakage occurred, in the present example, no such leakage occurred. In other words, it is evident that by producing the member (B) as a two layered structure formed from two soft materials (s) with different tensile modulus of elasticity values, the ability of the micro chemical device to withstand rupture is improved.

Example 8

This example presents an example of the first embodiment of the present invention in which a sheet formed from a medium hard material (m) is laminated onto the surface of the portion corresponding with the cavity section formed from a soft material (s).

[Preparation of a Micro Chemical Device]

A micro chemical device [#8] with a compression mechanism was prepared in the same manner as the example 2, with the exceptions that (1) the radiation-curable composition [e2] was used instead of the radiation-curable composition [e1], (2) a OSPS sheet [m2] of thickness 40 µm, which represents a medium hard material (m), was used instead of the OPP sheet, and (3) after formation of the member (B), the sheet was not peeled off, but was rather used as the micro chemical device in a laminated and bonded state.

The tensile characteristics of the OSPS sheet [m2] are shown in Table 1.

[Channel Opening and Closing Test]

When tests were conducted in the same manner as the example 7, the same effects as the example 7 were achieved. In other words, it is evident that by laminating a sheet formed from a medium hard material (m) onto the surface of the portion corresponding with the cavity section formed from the soft material (s), the ability of the micro chemical device to withstand rupture is improved.

Example 9

This example presents an example of the first embodiment of the present invention in which the member (A) with a groove is formed from a soft material (s) and the member (B) is formed from a medium hard material (m), and the cavity section is compressed from the side of the member (A).

[Preparation of the Member (A)]

The radiation-curable composition [e6] was applied to the corona discharge treated surface of a temporary base material comprising an OPP sheet (not shown in the drawings) using a 127 µm bar coater, and subsequently subjected to a 3 second irradiation of ultraviolet light of strength 50 mW/cm$^2$ using a multilight 200 type exposure apparatus light source unit manufactured by Ushio Inc., to cure the coating. Subsequently, more of the radiation-curable composition [e6] was applied to the surface of the cured coating using a 127 µm bar coater, and in a nitrogen atmosphere, all of the layer except for those portions corresponding with the groove (2) and the concave section (3) shown in FIG. 1 was irradiated through a photomask using a 3 second irradiation of the same ultraviolet light as described above. By subsequently washing and removing the uncured sections of the radiation-curable composition [e6] using acetone, a member [A9] of similar form to that shown in FIG. 1, comprising a groove (2) with a substantially rectangular cross section in which both the bottom and the side wall surfaces are formed from the radiation-curable composition [e6], and a circular cylindrical concave section (3), but without the inlet (4) and the outlet (5), was prepared. The dimensions of the groove included a width of 108 µm and a depth of 75 µm, and the dimensions of the concave section (3) displayed a diameter of 200 µm and a height of 75 µm.

[Preparation and Bonding of the Member (B)]

The radiation-curable composition [e7] was applied to a flat plate with dimensions of 2.5 cm×5 cm×thickness 2 mm formed from an acrylic resin [m3] and with holes of diameter 0.5 mm for forming an inlet (4) and an outlet (5) opened in positions corresponding with the two ends of the groove in the member [A9], using a 50 µm bar coater, and in an atmosphere of nitrogen, the entire composition except for those holes formed for the inlet (4) and the outlet (5) was then subjected to a 2 second irradiation of the same ultraviolet light of strength 50 mW/cm$^2$ as described above, thereby forming an incompletely cured coating with no fluidity. The uncured sections of resin were washed and removed. The incompletely cured coating surface was then bonded to the surface of the member [A9] in which the groove had been formed, and by subjecting the coating to a further 30 seconds of irradiation with the same ultraviolet light of strength 50 mW/cm$^2$ from the acrylic resin plate side of the structure to complete the curing of the coating, the member [B9] was bonded to the surface of the member [A9], and a capillary type channel (2) and a cavity section (3) formed partway along this channel were formed. Subsequently, a micro chemical device [#9] of the same form as the device shown in FIG. 1 was prepared, with the exceptions that the OPP sheet was peeled away from the member [A9], forming the inlet (4) and the outlet (5) on the member [B9], and the fact that the member (B) was a two layer structure formed from a cured product of the radiation-curable composition [e7] and the acrylic plate.

[Tensile Characteristics of the Members]

In a separate preparation, cured sheets of the radiation-curable composition [e6] and the radiation-curable composition [e7] were prepared, and the tensile characteristics were measured. The results are shown in Table 1. From Table 1 it is clear that the cured product of [e6] is a soft material (s), whereas the cured product of [e7] is a medium hard material (m).

[Hydrophilicity Tests]

The water contact angles at 25° C. for separately prepared cured coatings of the radiation-curable compositions [e6] and [e7] were 12 degrees and 15 degrees respectively.

[Biological Matter Adsorption Tests]

The radiation-curable compositions [e6] and [e7] were used to coat the inner surfaces of each well of a 96 well microtiter plate. A 0.5 µg/ml horseradish peroxidase solution ("ABTS Substrate Kit Horseradish Peroxidase" enzyme solution, from Vector Laboratories), which represents an enzyme for adsorption, was injected into the wells and left to stand for 30 minutes at 25° C., and then washed 3 times with distilled water. Subsequently, a substrate solution ("ABTS Substrate Kit Horseradish Peroxidase" ABTS substrate, from Vector Laboratories) was injected into the wells, left to stand for 30 minutes at 25° C., and then washed 3 times with distilled water. The absorbance at a wavelength of 405 nm was then measured, and produced results of 0.14 for [e6] and 0.16 for [e7]. In contrast and as a comparative test, a non-coated microtiter plate was subjected to the same test and yielded an absorbance result of 1.5. In other words, because the absorbance values in these tests show the quantity of adsorption (this test is commonly known as the ELISA method), it is evident that the coatings of [e6] and [e7] suppress the quantity of enzyme adsorption to approximately 1/10.

[Preparation of a Compression Mechanism]

The spring type clamp prepared in the example 1 was used.

[Channel Opening and Closing Test]

With the exception of positioning the protruding section of the spring type clamp on the side of the member (A) and compressing the position corresponding with the cavity section, tests were conducted in the same manner as the example 1, and the same effects as the example 1 were achieved.

Example 10

This example presents an example of a device with a base material, according to the second embodiment of the present invention.

[Preparation of a Member (A)]

The radiation-curable composition [e1] was applied to the surface of a base material (31) comprising a flat plate of dimensions 2.5 cm×5 cm×thickness 3 mm formed from polystyrene [m1] using a 127 μm bar coater, and subsequently subjected to a 3 second irradiation of ultraviolet light of strength 50 mW/cm$^2$ in a nitrogen atmosphere using a multilight 200 type light source unit manufactured by Ushio Inc., thereby forming a semi cured coating with no fluidity.

Subsequently, more of the radiation-curable composition [e1] was applied to the surface of the semi cured coating using a 127 μm bar coater, and in a nitrogen atmosphere, all of the layer except for those portions corresponding with a channel (32) and a cavity section (33) shown in FIG. 5 was irradiated through a photomask using a 3 second irradiation of the same ultraviolet light as described above, thereby semi curing the irradiated portions. The non-irradiated, uncured sections of the radiation-curable composition [e1] were washed and removed using a 50% aqueous solution of ethanol.

Figure 5A:
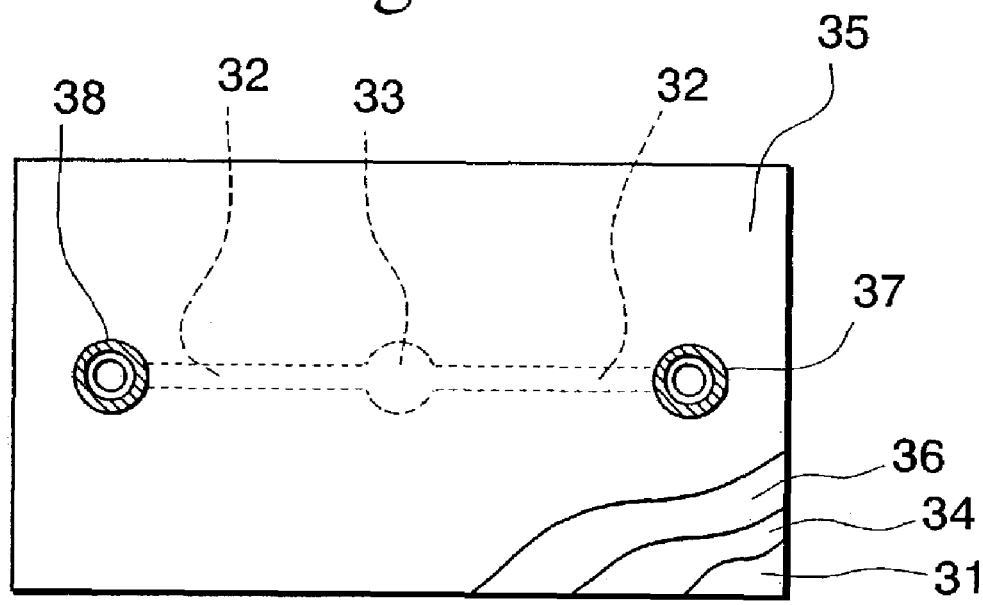
FIG. 5 is a schematic illustration of a plan view A, and a schematic illustration of an elevation B, of a micro chemical device prepared in an example 10.
Figure 5B:
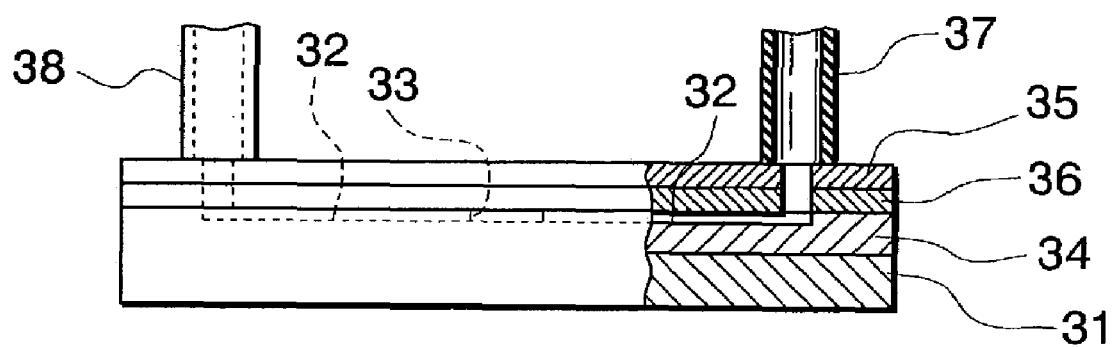

Using the above operation, a sheet type member (A) (34) of thickness 192 μm of the form shown in FIG. 5, formed from a soft material (s) comprising a cured product of the radiation-curable composition [e1], and comprising a groove (32) of width 104 μm, depth 96 μm and length 30 mm with a substantially rectangular cross section and with rounded corners at the bottom of the groove, and a circular cylindrical concave section (34) of diameter 200 μm and depth 96 μm with rounded corners at the bottom of the section formed partway along the groove, was bonded onto the top of the base material (31).

[Bonding of a Member (B)]

The radiation-curable composition [e5] was applied to an OPS sheet [m4] (35) using a 50 μm bar coater, and subsequently subjected to a 1 second irradiation of the same ultraviolet light described above in a nitrogen atmosphere, thereby forming a semi cured adhesive layer (36).

The surface of this adhesive layer (6) was bonded to the surface of the member (A) (34) prepared above in which the groove (32) had been formed, and by subjecting the coating to a further 30 seconds of irradiation with the same ultraviolet light to complete the curing of the adhesive layer (36), a sheet type member (B) comprising the OPS sheet [m4] (35) which represents a medium hard material (m) and the adhesive layer (36) with a thickness of approximately 30 mm which also represents a medium hard material (m), was formed and bonded to the surface of the member (A) (34), thereby forming a capillary type channel (32) and a cavity section (3) formed partway along the channel between the two members.

[Formation of an Inlet Channel and an Outlet Channel]

Subsequently, drill holes of diameter 0.5 mm were opened in the member (B) (35, 36) at both ends of the channel (32), and by bonding a polyvinyl chloride tube of diameter 3 mm to each of these holes, an inlet channel (37) and an outlet channel (38) were formed, thereby completing the preparation of a micro chemical device [#10] of the form shown in FIG. 5.

[Tensile Characteristics of the Member (A) and the Member (B)]

In a separate preparation, cured sheets of the radiation-curable composition [e1] and the radiation-curable composition [e5] were prepared, and the tensile characteristics were measured. The results are shown in Table 1, together with the results for the polystyrene [m1] and the OPS sheet [m4] used. From Table 1 it is clear that the cured product of the radiation-curable composition [e6] is a soft material (s), whereas the polystyrene [m1], the OPS sheet [m4], and the cured product of the radiation-curable composition [e7] are all medium hard materials (m).

[Preparation of a Compression Mechanism]

A spring type clamp compression device identical with that prepared in the example 1 was used.

[Channel Opening and Closing Test]

When water colored with methylene blue (manufactured by Wake Pure Chemical Industries, Ltd.) was injected into the channel via the inlet channel (37) using a microsyringe, the water exited from the outlet channel (38). Next, using the spring type clamp (11) prepared above, the portion corresponding with the cavity section (33) of the micro chemical device [#10] was compressed from the side of the member (B) (5, 6) using the protruding section of the clamp, and the water flow was interrupted, and when the clamp was released the channel was reopened. At this time, although a slight degree of deformation remained in the member (A) and the member (B), no rupture of the members was observed. The test was repeated 10 times, and the same effects were observed on each occasion.

Example 11

This example presents an example of a device without a base material, according to the second embodiment of the present invention.

[Preparation of a Micro Chemical Device]

With the exception of using an OPP sheet ("FOR", manufactured by Futamura Chemical Industries Co., Ltd., thickness 30 μm) instead of the polystyrene plate of the base material (31), a precursor for a micro chemical device [#11] with the same structure as the micro chemical device [#10] was formed in the same manner as the example 10, and the base material (31) was then peeled off, thereby completing the preparation of a micro chemical device [#11] with the same structure as that shown in FIG. 5, except for the absence of the base material (31).

[Preparation of a Compression Mechanism]

A brass rod with the tip cut to a hemispherical shape of radius 0.25 mm was prepared as a compression mechanism.

[Channel Opening and Closing Test]

With the exceptions of conducting the compression operation with the micro chemical device placed on top of a glass plate with the member (A) facing downward, using the brass rod type compression mechanism instead of the clamp type compression mechanism, and compressing the portion of the member (B) corresponding with the cavity section manually, tests were conducted in the same manner as the example 10, and the same effects as the example 10 were achieved.

Example 14

This example presents an example of a device without a base material, according to the second embodiment of the present invention.

[Preparation of a Member (A)]

A hot pressed sheet of dimensions 2.5 cm×5 cm×thickness 500 μm formed from thermoplastic polyurethane [s1] was heated with an electric hot air torch to soften the surface, subsequently pressed onto a glass template (not shown in the drawings) heated to a temperature of 150° C. and then cooled, and then peeled off the template, thereby forming in the surface of the sheet, a groove (2) of width 30 μm, depth 30 μm and length 30 mm with a substantially rectangular cross section and with rounded corners at the bottom of the groove, and a circular cylindrical concave section (33) of diameter 90 μm and depth 30 μm formed partway along the groove, with rounded corners at the bottom of the section, thereby completing preparation of the member (A) (34).

[Bonding of a Member (B)]

A sheet type member (B) (35, 36) of the same structure as the example 10 was formed in the same manner as the example 10, and then bonded to the surface of the member (A) (34) prepared above, thereby forming a capillary type channel (32) and a cavity section (33) formed partway along the channel between the two members, and completing the preparation of a precursor of a micro chemical device [#14].

[Formation of an Inlet Channel and an Outlet Channel]

By subsequently opening drill holes of diameter 0.5 mm in the member (B) (35, 36) at both ends of the channel (32), an inlet channel (37) and an outlet channel (38) were formed, thereby completing the preparation of a micro chemical device [#14] of the same form as that shown in FIG. 5, except for the absence of the base material (31).

[Tensile Characteristics of the Member (A) and the Member (B)]

In a separate preparation, the tensile characteristics of the hot pressed sheet formed from the thermoplastic polyurethane [s1] were measured. The results are shown in Table 1.

From Table 1 it is clear that the thermoplastic polyurethane [s1] used is a soft material (s).

[Channel Opening and Closing Test]

Tests were conducted in the same manner as the example 11, and the same effects as the example 11 were achieved.

Example 15

This example presents an example of the third embodiment of the present invention, in which a member (C) is formed from a medium hard material (m), a member (D) which becomes the side walls of the channel is formed from a soft material (s), and a member (B) is formed from a soft material (s).

[Preparation of a Member (C) and a Member (D)]

The radiation-curable composition [e7] was applied to the surface of a flat plate of dimensions 2.5 cm×5 cm×thickness 2 mm formed from the acrylic resin [m3] using a 127 μm bar coater, and subsequently subjected to a 30 second irradiation of ultraviolet light of strength 50 mW/cm$^2$ in a nitrogen atmosphere using a multilight 200 type exposure apparatus light source unit manufactured by Ushio Inc., thereby curing the composition, and forming an acrylic resin member (C) with a cured coating of the radiation-curable composition [e7] provided on the surface.

Subsequently, the radiation-curable composition [e8] for forming the member (D) was applied to the top of the coated member (C), and in a nitrogen atmosphere, all of the composition layer except for those portions corresponding with the channel (2) and the cavity section (3) shown in FIG. 1 was irradiated through a photomask using a 30 second irradiation of the same ultraviolet light as described above, thereby formed a cured product of the radiation-curable composition [e8]. By subsequently washing and removing the uncured sections of the radiation-curable composition [e8] using acetone, a member (D) with a resin lacking section was formed. An inlet (4) and an outlet (5) were then formed at both ends of the resin lacking section (2) of the member (D) by opening drill holes of diameter 0.5 mm in the member (C) and the resin member (D). The above operation enabled the preparation of a composite member [CD18] with a similar form to that shown in FIG. 1, but comprising a layered product of the member (C) and the member (D) instead of the member (A), in which the resin lacking section comprises a lacking section (2) of width 108 μm and depth 67 μm [in other words, the thickness of the member (D)] with a substantially rectangular cross section for forming a channel, a circular cylindrical lacking section (3) of diameter 200 μm and height 67 μm for forming a cavity section, an inlet (4) and an outlet (5).

[Bonding of a Member (B)]

The radiation-curable composition [e6] was applied to the corona treated surface of an OPP sheet (not shown in the drawings) using a 127 μm bar coater, and subsequently subjected to a 3 second irradiation of the same ultraviolet light as described above to semi cure the composition, and the surface of this coating was then bonded to the surface of the member [D]. Subsequently, by subjecting the structure to a further 30 seconds of irradiation with the same ultraviolet light from the OPP sheet side of the structure to complete the curing of the coatings of the radiation-curable compositions [e7], [e8] and [e6], and then peeling off the OPP sheet, a micro chemical device [#15] of a similar form to that shown in FIG. 1 was prepared, with the exception that the bottom of the channel and the side surfaces of the channel were formed from different members.

[Preparation of a Compression Mechanism]

The spring type clamp prepared in the example 1 was used.

[Channel Opening and Closing Test]

Tests were conducted in the same manner as the example 1, and with the exception that a more reliable complete closure of the valve than the example 1 was possible, the same effects as the example 1 were achieved.

Example 16

This example presents an example of the third embodiment of the present invention, with a structure in which the height of the cavity section is shallower than the height of the channel.

[Preparation of a Micro Chemical Device]

Figure 3:
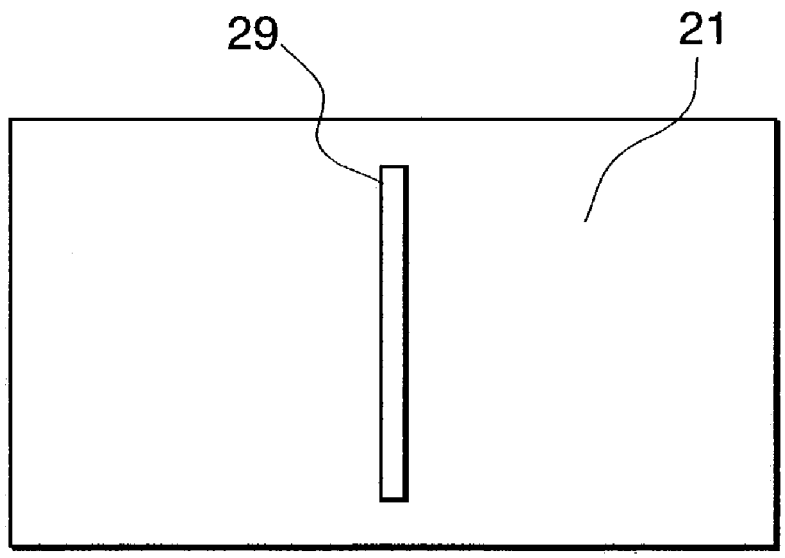
FIG. 3 is a schematic illustration of a plan view of a member (C) partway through production of a micro chemical device prepared in an example 16.

Drill holes of diameter 0.5 mm were opened at positions equivalent to the two ends of a channel (23, 28) in a flat plate type substrate (21) of dimensions 2.5 cm×5 cm×thickness 3 mm formed from the polystyrene [m1], thereby forming an inlet (25) and an outlet (26). With the underside of the inlet (25) and the outlet (26) blocked with a masking tape used for painting, the substrate was then coated with a radiation-curable composition [e4] using a 127 μm bar coater, and subsequently, the portion to become a raised bottom section (29) was subjected to a 10 second irradiation of ultraviolet light of 50 mW/cm$^2$ through a photomask, using a multilight 200 type exposure apparatus light source unit manufactured by Ushio Inc. Next, the uncured sections of the composition were washed and removed with acetone, forming the raised bottom section (29) of width 480 μm, length 10 mm and thickness 103 μm shown in FIG. 3, and completing the preparation of a member [C16] of the form shown in FIG. 3.

Figure 4:
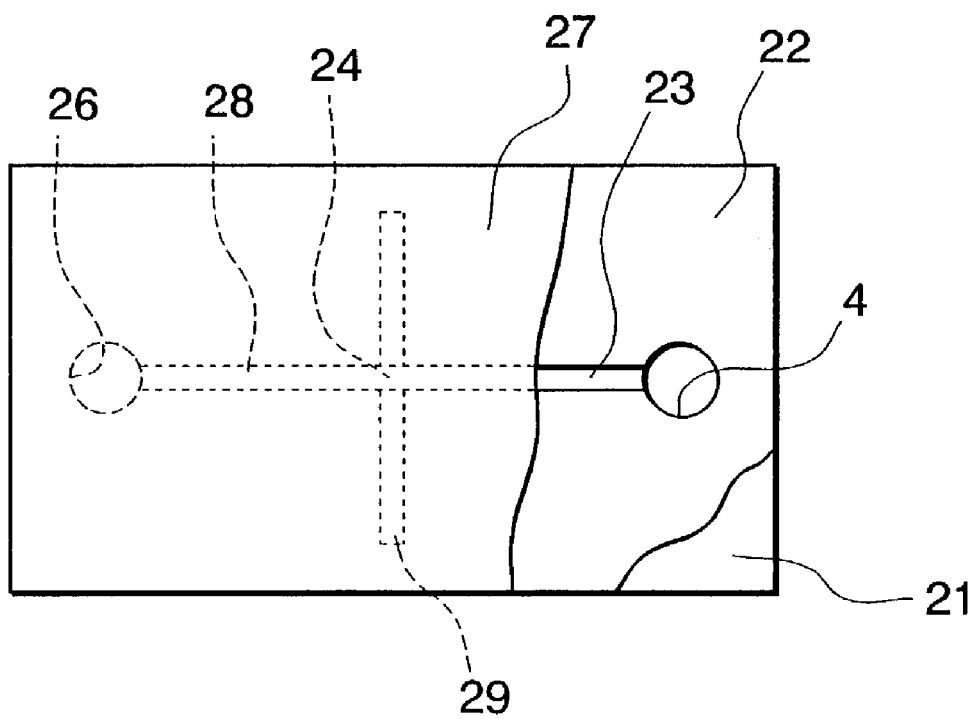
FIG. 4 is a schematic illustration of a partial sectional plan view of a micro chemical device prepared in the example 16.

With the underside of the inlet (25) and the outlet (26) of the member [C16] blocked, the radiation-curable composition [e3] was applied to the surface of the substrate (21) so as to cover the raised bottom section (29), and 15 glass rods of diameter of approximately 200 μm and length approximately 1.5 mm (produced in-house, not shown in the figures) were then used as spacers and positioned on those sections other than the portions to become the groove (23, 28), the cavity section (24), the inlet (25) and the outlet (26). The substrate and rods were then covered with a member [B10] formed from a hot pressed sheet of thickness approximately 500 μm formed from the polyurethane [s1], which is a soft material (s), and subsequently, in a nitrogen atmosphere, the entire sheet except those portions to become the groove (23, 28), the cavity section (24), the inlet (25) and the outlet (26) were subjected to a 10 second irradiation through a photomask with the same ultraviolet light of 50 mW/cm$^2$ as described above. Following completion of this ultraviolet irradiation, by applying suction at the outlet (25) and washing with acetone, the uncured sections of the radiation-curable composition [e3] were removed, thereby completing the preparation of a micro chemical device [#16] of the form shown in FIG. 4 with a groove of width 480 μm and depth 190 μm, and a cavity section (24) of width 480 μm, length 480 μm and depth 87 μm shaped as a rectangle when viewed from above.

[Preparation of a Compression Mechanism]

With the exceptions of forming the tip of the screw as a hemispherical shape of radius 1 mm, and adjusting the amount of protrusion of the screw to 1 mm, a similar spring type clamp to that of the example 1 was prepared, and used.

[Channel Opening and Closing Test]

Tests were conducted in the same manner as the example 1, and the same effects as the example 1 were achieved.

Example 17

Micro chemical devices [#17-1 to 17-6] were prepared in the same manner as the example 16, with the exceptions of using (1) the polyurethane [s2], (2) the PVC [s3], (3) the EVA [s4], (4) the polyamide elastomer [s5], (5) the polyester elastomer [s6], or (6) the modified polyolefin [s7] respectively, instead of the polyurethane [s1], and preparing the compression mechanism in the same manner as the example 7.

[Channel Opening and Closing Tests]

For each of the micro chemical devices [#17-1 to 17-6], tests were conducted in the same manner as the example 7, and in each case the same effects as the example 7 were achieved.

Example 18

This example presents an example of the third embodiment of the present invention, in which the member (C) is formed from a medium hard material (m), the member (D) which forms the wall sections of the groove is formed from a medium hard material (m), and the member (B) is formed from a soft material (s).

[Preparation of Members (C) and (D)]

With the exception of using the composition [e7] instead of the composition [e6] as the radiation-curable composition for forming the member (D), formation of the members was conducted in the same manner as the example 15, and a micro chemical device [#18] with the same structure as the micro chemical device [#15] was then prepared, with the exception that the member (D) was formed from a cured product of the radiation-curable composition [e7].

[Hydrophilicity Tests]

The water contact angles at 25° C. for separately prepared cured coatings of the radiation-curable compositions [e6], [e7] and [e8] were 12 degrees, 15 degrees and 13 degrees respectively.

[Preparation of a Compression Mechanism]

The spring type clamp prepared in the example 1 was used.

[Channel Opening and Closing Test]

Opening and closing tests were conducted in the same manner as the example 1, and the same effects as the example 1 were achieved.

Example 19

This example presents an example of the fourth embodiment of the present invention, in which the member (C) is formed from a soft material (s), the member (D) which forms the side walls of the channel is formed from a soft material (s), and the member (B) is formed from a medium hard material (m).

[Preparation of the Members (C) and (D)]

The radiation-curable composition [e6] was applied to the surface of a temporary base material comprising an OPP sheet using a 127 µm bar coater, and subsequently subjected to a 3 second irradiation of ultraviolet light of 50 mW/cm² in an atmosphere of nitrogen, using a multilight 200 type light source unit manufactured by Ushio Inc., thereby forming a semi cured coating for forming the member (C) (41).

Figure 6A:
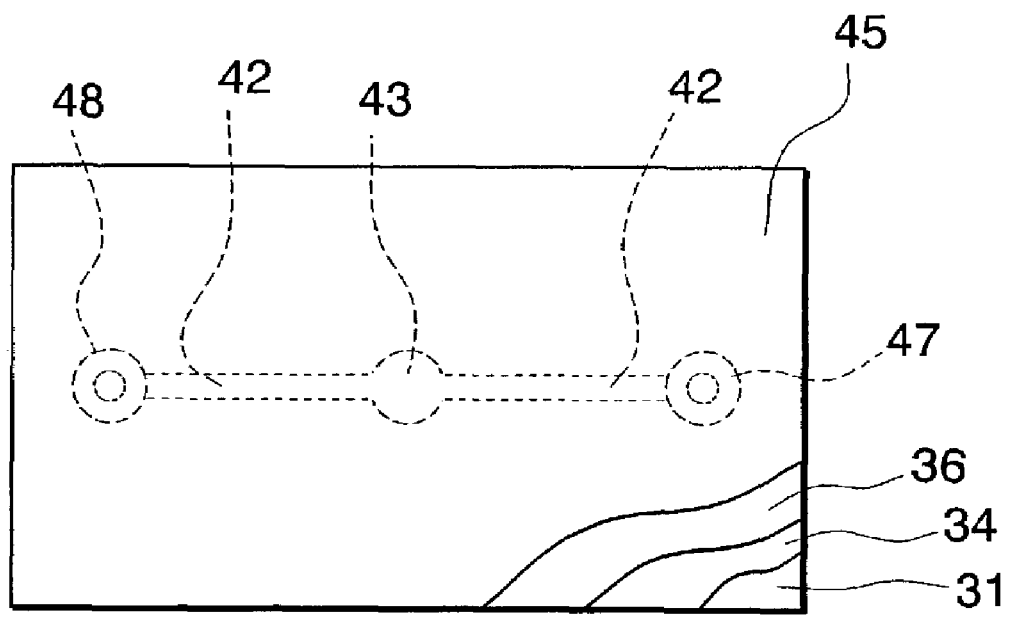
FIG. 6 is a schematic illustration of a plan view A, and a schematic illustration of an elevation B, of a micro chemical device prepared in examples 19 and 20.
Figure 6B:
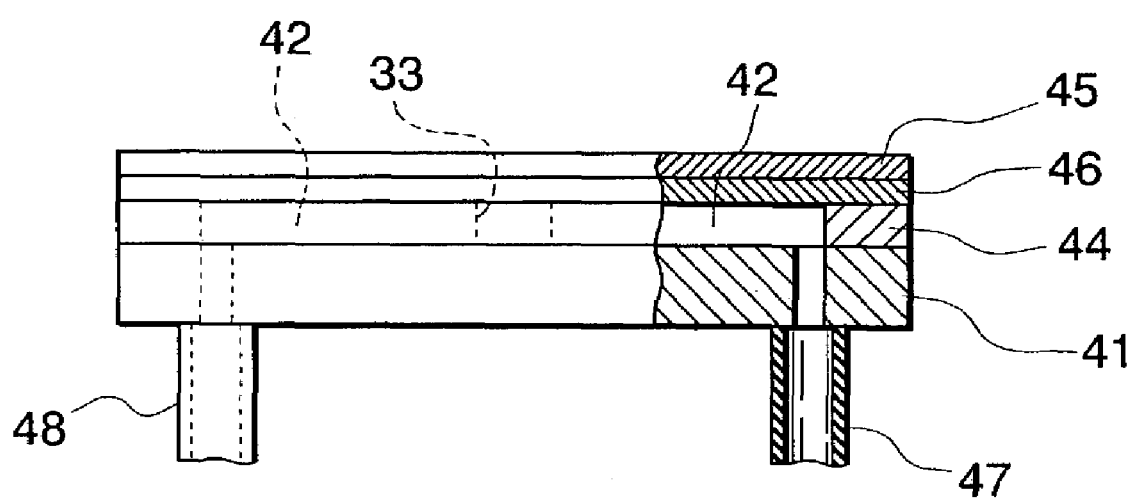
Figure 7A:
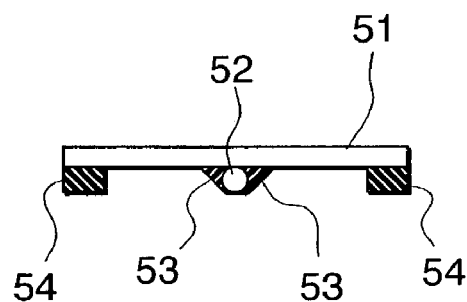
FIG. 7 is a schematic illustration of a plan view A, and a schematic illustration of an elevation B, of a member (H) used in examples 5, 24, 25, 26 and 27.
Figure 7B:
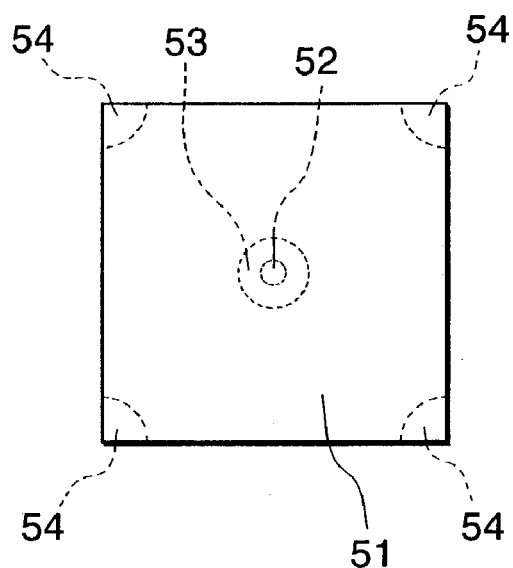
Figure 8:
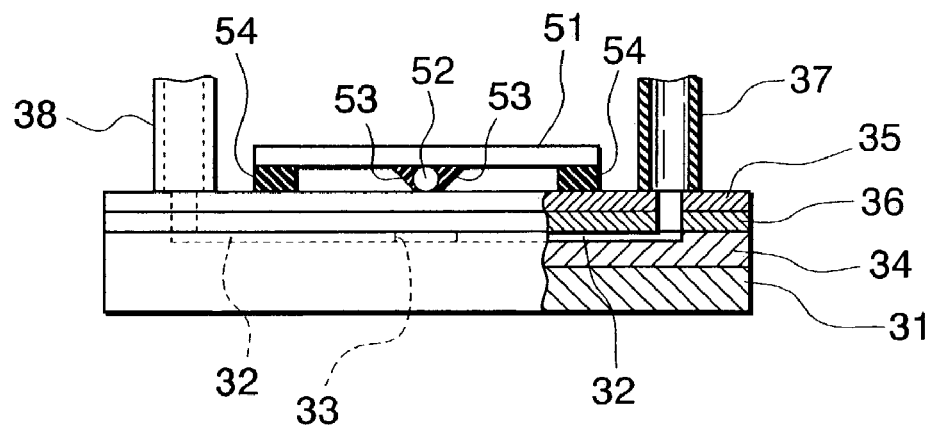
FIG. 8 is a schematic illustration of an elevation of a micro chemical device in which a member (H) is mounted on [#19] and [#20] in the example 24.

The radiation-curable composition [e8] was then applied to the surface of this semi cured coating using a 127 µm bar coater, and all of the composition layer except for those portions corresponding with a channel (42) and a cavity section (43) of the form shown in FIG. 6 was irradiated through a photomask using a 3 second irradiation of the same ultraviolet light as described above, thereby converting the irradiated portions to a semi cured coating and forming the member (C). The thickness of the member (D) (44) was 96 µm.

The non-irradiated, uncured sections of the radiation-curable composition [e8] were removed using a 50% aqueous solution of ethanol, forming a member (D) (44) comprising a layer (44) with lacking sections for forming the channel (42) and the cavity section (43). The dimensions of the resin lacking section for forming the channel (42) included a width of 104 µm, a depth of 96 µm and a length of 30 mm. The resin lacking section for forming the cavity section (43) provided partway along the channel was a circular cylindrical shape of diameter 200 µm and depth 96 µm. The thickness of the member (D) (44) was 96 µm.

[Bonding of the Member (B)]

In a similar manner to the preparation of the member (C), the radiation-curable composition [e7] was applied to a temporary base material formed from an OPP sheet, and the entire composition layer was then irradiated for 3 seconds using the same ultraviolet light as described above to form a member (B) formed from a semi cured composition. With the member (B) positioned in close contact with the member (D), all of the members were then subjected to a 30 second irradiation with the same ultraviolet light described above, thereby completely curing all of the member (C), the member (D) and the member (B) and bonding the members together, forming a capillary type channel (42) and a cavity section (43). Subsequently, the temporary base material OPP sheets were peeled away from the member (C) and the member (B).

Subsequently, drill holes of diameter 0.5 mm were opened in the member (C) (41) at both ends of the channel (42); and a polyvinyl chloride tube of diameter 3 mm was bonded to each of these holes, forming an inlet channel (47) and an outlet channel (48), and thereby completing the preparation of a micro chemical device [#19] of the form shown in FIG. 6.

[Hydrophilicity Tests]

Before bonding the polyvinyl chloride tube to the inlet channel (47), the inlet channel (47) was positioned facing upwards, and when a drop of distilled water was placed in the inlet channel (47), the distilled water was spontaneously drawn into the inlet channel (47), filling the channel (42) and the cavity section (43) and reaching the outlet channel (48). This observation indicates that the water contact angle on the internal surfaces of the channel is extremely low.

The water contact angles at 25° C. for separately prepared cured coatings of the radiation-curable compositions [e6], [e7] and [e8] were 12 degrees, 15 degrees and 13 degrees respectively.

[Channel Opening and Closing Test]

Channel opening and closing tests were conducted in the same manner as the example 10, by compressing the cavity section from the side of the member (B) of the micro chemical device [#19], and the same effects as the example 10 were achieved.

Example 20

This example presents an example of the fifth embodiment of the present invention.

[Preparation of Members (C) and (D)]

The radiation-curable composition [e1] was applied to the surface of a member (C) (41) comprising a flat plate of dimensions 2.5 cm×5 cm×3 mm formed from the polystyrene [m1] using a 127 µm bar coater, and in a nitrogen atmosphere, all of the composition layer except for those portions corresponding with a channel (42) and a cavity section (43) shown in FIG. 6 was irradiated for 3 seconds with ultraviolet light of 50 mW/cm² through a photomask using a multilight 200 type light source unit manufactured by Ushio Inc., thereby forming a coating with the irradiated sections in a semi cured state.

The non-irradiated, uncured sections of the radiation-curable composition [e1] were removed using a 50% aqueous solution of ethanol, forming a member (D) (44) comprising a layer with resin lacking sections for forming the channel (42) and the cavity section (43). The dimensions of the resin lacking section for forming the channel (42) included a width of 104 µm, a depth of 96 µm and a length of 30 mm. The resin lacking section for forming the cavity section (43) provided partway along the channel was a circular cylindrical shape of diameter 200 µm and depth 96 µm. The thickness of the member (A) (44) was 96 µm.

[Bonding of the Member (B)]

In a similar manner to the example 10, an OSPS sheet [m2] (45) was bonded to the surface of the member (D) (44) using a cured product of the radiation-curable composition [e5] as an adhesive layer, thereby forming the capillary type channel (42) and the cavity section (43), while also combining the biaxially stretched OSPS sheet [m2] (45) and the adhesive layer (46) to form the member (B).

[Formation of an Inlet Channel and an Outlet Channel]

Subsequently, drill holes of diameter 0.5 mm were opened in the member (C) (41) at both ends of the channel (42), and a polyvinyl chloride tube of diameter 3 mm was bonded to each of these holes, forming an inlet channel (47) and an outlet channel (48), and completing the preparation of a micro chemical device [#20] of the form shown in FIG. 6.

[Channel Opening and Closing Test]

Tests were conducted in the same manner as the example 10, and the same effects as the example 10 were achieved.

Example 21

This example presents an example of the fifth embodiment of the present invention, in which the members (B), (C) and (D) are all hydrophilic materials.

[Preparation of a Micro Chemical Device]

With the exceptions that the member (C) was formed from a cured product of the radiation-curable composition [e7], the member (D) was formed from a cured product of the radiation-curable composition [e8], and the member (B) was formed from a cured product of the radiation-curable composition [e7], a micro chemical device [#21] was prepared in the same manner as the example 25.

[Channel Opening and Closing Test]

Tests were conducted in the same manner as the example 25, and the same effects as the example 3 were achieved.

Example 22

This example presents an example of an embodiment in which a member (H) with a screw type convex structure is fixed to the surface of the member (B).

[Preparation of a Compression Mechanism]

A compression mechanism of identical construction to the plate type member [H2] with a screw attached prepared in the example 2 was prepared and used.

[Preparation of Micro Chemical Devices]

A screw was fixed to the surface of the member (B) in each of the micro chemical devices [#10] and [#16] prepared in the examples 10 and 16, with the tip of the screw fixed in a position corresponding with the cavity section in each case, thereby forming micro chemical devices with a screw type compression mechanism.

[Channel Opening and Closing Test]

Tests using these micro chemical devices were conducted in the same manner as the example 2, and the same effects as the example 2 were achieved in each case.

Example 23

This example presents an example of an embodiment in which a compression mechanism comprising a convex structure is provided on the surface of the member (B).

[Preparation of Micro Chemical Devices]

A glass sphere with a diameter of 0.5 mm was bonded onto the surface of the member (B) of each of the micro chemical devices [#10], [#11], [#14], [#16], [#18] and [#19] prepared in the examples 10, 11, 14, 16, 18 and 19, in a position corresponding with the cavity section in each case, using the radiation-curable composition [e4] as an adhesive, thereby forming micro chemical devices with a convex structure compression mechanism.

[Channel Opening and Closing Test]

Tests using these micro chemical devices were conducted in the same manner as the example 3, and the same effects as the example 3 were achieved in each case.

Example 24

This example presents an example of the fifth embodiment of the present invention in which a sheet type member (H) with a convex structure provided on the surface is fixed to the surface of the micro chemical device with the convex structure facing inwards.

[Preparation of Micro Chemical Devices]

Sheet type members (H) with a convex structure similar to that prepared in the example 5 were prepared, and these were fixed to the surface of the member (B) of each of the micro chemical devices [#10], [#11], [#14], [#16], [#18] and [#19] prepared in the examples 10, 11, 14, 16, 18 and 19, with the convex structure facing towards the cavity section and in a position corresponding with the cavity section, and the four corners of each member (H) were then bonded to the member (B) using the radiation-curable composition [e4], thereby forming micro chemical devices with a compression mechanism.

[Channel Opening and Closing Test]

Tests using these micro chemical devices were conducted in the same manner as the example 5, and the same effects as the example 3 were achieved in each case.

Example 25

This example presents an example of the fifth embodiment of the present invention in which a sheet type member (H) with a convex structure provided on the surface is fixed to the surface of the micro chemical device with the convex structure facing outwards.

[Preparation of Micro Chemical Devices]

Using a sheet type member (H) with a convex structure similar to that of the example 33, micro chemical devices with a compression mechanism were prepared in the same manner as the example 33, with the exception that the member (H) was fixed to the member (B) with the convex structure facing away from the cavity section.

[Channel Opening and Closing Test]

Tests using these micro chemical devices were conducted in the same manner as the example 3, and the same effects as the example 3 were achieved in each case.

Example 26

This example presents an example of a micro chemical device with a convex structure on the surface comprising a member (A) formed from a soft material (s) and a member (B) formed from a soft material (s), as well as a micro chemical device comprising a member (A) formed from a soft material (s) and a member (B) formed from a soft material (s), with a sheet type member (H) provided with a convex structure on the surface fixed to the top of the member (B).

[Preparation of a Micro Chemical Device Precursor]

A micro chemical device precursor [#26P] was prepared in the same manner as example 1, with the exception of forming both the member (A) and the member (B) from a cured product of the radiation-curable composition [e6].

[Preparation of a Micro Chemical Device Precursor]

With the exception of using [#26P] as the micro chemical device precursor, a micro chemical device [#26-1] with a convex structure provided on the surface of the member (B) in a position corresponding with the cavity section was prepared in the same manner as the example 23, in the same manner as the example 14. Furthermore, in a similar manner, a micro chemical device [#26-2] with a convex structure provided on the surface of the member (A) in a position corresponding with the cavity section was also prepared.

Furthermore, with the exception of using [#26P] as the micro chemical device precursor, a micro chemical device [#26-3] with a convex structure fixed to the surface of the member (B) in a position corresponding with the cavity section and with the convex structure facing inwards was prepared in the same manner as the example 24. Furthermore, in a similar manner, a micro chemical device [#26-4] with a member (H) fixed on the side of the member (A) was also prepared.

In addition, with the exception of using [#26P] as the micro chemical device precursor, a micro chemical device [#26-5] with a convex structure fixed to the surface of the member (B) in a position corresponding with the cavity section but with the convex structure facing away from the cavity section was prepared in the same manner as the example 25. Furthermore, in a similar manner, a micro chemical device [#26-6] with a member (H) fixed on the side of the member (A) was also prepared.

[Channel Opening and Closing Test]

Tests using these micro chemical devices were conducted in the same manner as the examples 23, 24 and 25, and the same effects were achieved in each case.

Example 27

This example presents an example of a micro chemical device with a convex structure on the surface, in which the member (B), the member (C) and the member (D) are each formed entirely of a soft material (s), as well as a micro chemical device in which the member (B), the member (C) and the member (D) are each formed entirely of a soft material (s), and a sheet type member (H) provided with a convex structure is fixed to the surface of the member (B).

[Preparation of a Micro Chemical Device Precursor]

A micro chemical device precursor [#27P] was prepared in the same manner as the example 11 with the exception of forming the member (B), the member (C) and the member (D) entirely from a cured product of the radiation-curable composition [e6].

[Preparation of a Micro Chemical Device Precursor]

With the exception of using [#26P] as the micro chemical device precursor, a micro chemical device [#27-1] with a convex structure provided on the surface of the member (B) in a position corresponding with the cavity section was prepared in the same manner as the example 23, in the same manner as the example 14.

Furthermore, with the exception of using [#26P] as the micro chemical device precursor, a micro chemical device [#27-2] with a convex structure fixed to the surface of the member (B) in a position corresponding with the cavity section and with the convex structure facing inwards was prepared in the same manner as the example 24.

In addition, with the exception of using [#26P] as the micro chemical device precursor, a micro chemical device [#27-3] with a convex structure fixed to the surface of the member (B) in a position corresponding with the cavity section but with the convex structure facing away from the cavity section was prepared in the same manner as the example 25.

[Channel Opening and Closing Test]

Tests using these micro chemical devices were conducted in the same manner as the examples 23, 24 and 25, and the same effects were achieved in each case.

TABLE 1

| Material | Tensile modulus of elasticity MPa | Breaking elongation % |
|---|---|---|
| Cured product of the radiation-curable composition [e1] | 210 | 8.6 |
| Cured product of the radiation-curable composition [e2] | 110 | 6.3 |
| Cured product of the radiation-curable composition [e3] | 300 | 6.6 |
| Cured product of the radiation-curable composition [e4] | 500 | 24 |
| Cured product of the radiation-curable composition [e5] | 1610 | 2.8 |
| Cured product of the radiation-curable composition [e6] | 430 | 8.9 |
| Cured product of the radiation-curable composition [e7] | 1350 | 3.3 |
| Cured product of the radiation-curable composition [e8] | 120 | 6.2 |
| Polyurethane [s1] | 150 | 400 |
| Polyurethane [s2] | 15 | 600 |
| PVC [s3] | 35 | 350 |
| EVA [s4] | 110 | 700 |
| Polyamide elastomer [s5] | 38 | 400 |
| Polyester elastomer [s6] | 11 | 600 |
| Modified polyolefin [s7] | 600 | 500 |
| Polystyrene [m1] | 2800 | 3.6 |
| OSPS sheet [m2] | 3400 | |
| Acrylic resin [m3] | 2900 | |
| OPS sheet [m4] | 3000 | |
| (Reference) | | |
| Glass | approx. 70,000 | |
| Steel | approx. 200,000 | |

INDUSTRIAL APPLICABILITY

A micro chemical device of the present invention enables the opening and closing of a channel and the regulation of flow rate to be achieved with a simple structure. In a micro chemical device of the present invention, an independent fluid pump is not required for each device, and the fluid can be supplied using a common pressure, and consequently it is easier to conduct simultaneous parallel processing of a plurality of devices, meaning the operating efficiency can be improved. Furthermore, a micro chemical device of the present invention can also be applied to applications in which a plurality of fluids flow through a single chemical device, with the fluids supplied using a common pressure while the flow rate is regulated for each channel, and consequently the overall apparatus can be simplified. In addition, the present invention is able to provide a micro chemical device with a valve function, which has a simple structure and high pressure resistance, and in which the channel cross-sectional area does not depend on the fluid pressure, and which furthermore displays little adsorption of biological matter, as well as a flow regulation method using such a device.

The invention claimed is:

1. A micro chemical device with a valve function, in which a member (B) is bonded to a member (A) with a groove in the surface thereof, via the surface of the member (A) in which the groove is formed, a capillary type channel of width from 1 to 1000 μm and height from 1 to 1000 μm is formed by the groove of the member (A) and the member (B) at the bonding surface between the member (A) and the member (B), a cavity section is formed partway along the channel and the width of this cavity section is from 0.5 to 100 fold the width of the capillary type channel and the ratio of maximum height/maximum width for the cavity section is no more than 1, and either one of the member (A) and the member (B) is formed from a soft material with a tensile modulus of elasticity within a range from 0.1 MPa to 700 MPa, at least within the portion which corresponds with the position of the cavity section, wherein a member (H) comprising a convex structure is laminated to the outside of the member (A) or the member (B), and the convex structure is fixed in a position corresponding with the cavity section, with the convex structure facing the cavity section, and by selectively compressing the cavity section from the external surface on the member (A) side and/or the member (B) side, the volume of the cavity section can be reduced in a reversible manner.

2. A micro chemical device according to claim 1, wherein the member (H) comprises a sheet type member, and the convex structure is attached to the sheet type member.

3. A micro chemical with a valve function, in which a member (B) is bonded to a member (A) with a groove in the surface thereof, via the surface of the member (A) in which the groove is formed, a capillary type channel of width from 1 to 1000 μm and height from 1 to 1000 μm is formed by the groove of the member (A) and the member (B) at the bonding surface between the member (A) and the member (B), a cavity section is formed partway along the channel and the width of this cavity section is from 0.5 to 100 fold the width of the capillary type channel and the ratio of maximum height/maximum width for the cavity section is not more than 1, and either one of the member (A) and the member (B) is formed from a soft material with a tensile modulus of elasticity within a range from 0.1 MPa to 700 MPa, at least within the portion which corresponds with the position of the cavity section, wherein a member (H) comprising a convex structure is laminated on top of the member (B) with the convex structure facing away from the member (B), and is formed from a material with a tensile modulus of elasticity within a range from 10 MPa to 10 GPa, and with a thickness within a range from 0.5 to 500 μm and by selectively compressing the cavity section from the external surface on the member (A) side and/or the member (B) side, the volume of the cavity section can be reduced in a reversible manner.

4. A micro chemical device with a valve function, in which a member (B) is bonded to a member (A) with a groove in the surface thereof, via the surface of the member (A) in which the groove is formed, a capillary type channel of width from 1 to 1000 μm and height from 1 to 1000 μm is formed by the groove of the member (A) and the member (B) at the bonding surface between the member (A) and the member (B), a cavity section is formed partway along the channel and the width of this cavity section is from 0.5 to 100 fold the width of the capillary type channel and the ratio of maximum height/maximum width for the cavity section is not more than 1, and both the member (A) and the member (B) are formed from a soft material with a tensile modulus of elasticity within a range from 0.1 MPa to 700 MPa, at least within the portion which corresponds with the cavity section, and a convex structure is provided on the surface of the member (A) and/or the member (B), in a position corresponding with the cavity section, wherein by compressing the cavity section from the external surface of the member on which the convex structure is provided, the volume of the cavity section can be reduced in a reversible manner.

5. A micro chemical device with a valve function, in which a member (B) is bonded to a member (A) with a groove in the surface thereof, via the surface of the member (A) in which the groove is formed, a capillary type channel of width from 1 to 1000 μm and height from 1 to 1000 μm is formed by the groove of the member (A) and the member (B) at the bonding surface between the member (A) and the member (B), a cavity section is formed partway along the channel and the width of this cavity section is from 0.5 to 100 fold the width of the capillary type channel and the ratio of maximum height/maximum width for the cavity section is not more than 1, and both the member (A) and the member (B) are formed from a soft material with a tensile modulus of elasticity within a range from 0.1 MPa to 700 MPa, at least within the portion which corresponds with the cavity section, and a member (H) comprising a convex structure is laminated onto the member (A) and/or the member (B), or alternatively is laminated onto a sheet type member (E) with a thickness from 0.5 to 500 μm, which is formed from a medium hard material with a tensile modulus of elasticity within a range from 700 MPa to 10 GPa provided on the outside of the member (A) and/or the member (B), and the convex structure is fixed in a position corresponding with the cavity section, wherein by compressing the cavity section from the surface of the member with the convex structure, the volume of the cavity section can be reduced in a reversible manner.

6. A micro chemical device with a valve function, in which by bonding a member (B) and a member (C) together with a layer type member (D) comprising a lacking section for forming a channel disposed therebetween, a capillary type channel of width from 1 to 1000 μm and height from 1 to 1000 μm is formed between the member (B) and the member (C) by the lacking section of the material of the member (D), and a cavity section is formed partway along the channel and the width of this cavity section is from 0.5 to 100 fold the width of the capillary type channel and the ratio of maximum height/maximum width for the cavity section is not more than 1, and each of the members (B), (C) and (D) is formed from a soft material with a tensile modulus of elasticity within a range from 0.1 MPa to 700 MPa, at least within the portion which corresponds with the cavity section (or in the case of the member (D), the portion surrounding the cavity section), and a member (H) comprising a convex structure is provided on the surface of the member (B) in a position corresponding with the cavity section, wherein by compressing the cavity section from the surface of the member (B), the volume of the cavity section can be reduced in a reversible manner.

7. A micro chemical device with a valve function, in which by bonding a member (B) and a member (C) together with a layer type member (D) comprising a lacking section for forming a channel disposed therebetween, a capillary type channel of width from 1 to 1000 μm and height from 1 to 1000 μm is formed between the member (B) and the member (C) by the lacking section of the material of the member (D), and a cavity section is formed partway along the channel and the width of this cavity section is from 0.5 to 100 fold the width of the capillary type channel and the ratio of maximum height/maximum width for the cavity section is not more than 1, and each of the members (B), (C) and (D) is formed from a soft material with a tensile modulus of elasticity within a range from 0.1 MPa to 700 MPa, at least within the portion which corresponds with the cavity section (or in the case of the member (D), the portion surrounding the cavity section), and a member (H) comprising a convex structure is laminated onto the member (B), or alternatively is laminated onto a sheet type member (B) with a thickness from 0.5 to 500 μm, which is formed from a medium hard material with a tensile modulus of elasticity within a range from 700 MPa to 10 GPa provided on the outside of the member (B), and the convex structure is fixed in a position corresponding with the cavity section, wherein by compressing the cavity section from the surface of the member (B), the volume of the cavity section can be reduced in a reversible manner.

8. A micro chemical device according to any one of claims 1 and 3, wherein the soft material with a tensile modulus of elasticity within a range from 0.1 to 700 MPa, and/or the medium hard material with a tensile modulus of elasticity within a range from 700 MPa to 10 GPa are cured products of radiation-curable compositions.

9. A micro chemical device according to claim 8, wherein the radiation-curable composition comprises an amphipathic radiation-curable compound.

10. A micro chemical device according to any one of claims 1 and 3, wherein either one of the member (A) and the member (B) is formed from a soft material with a tensile modulus of elasticity within a range from 0.1 MPa to 700 MPa, at least within the portion which corresponds with the position of the cavity section, and the other member is formed from a medium hard material with a tensile modulus of elasticity of at least 700 MPa, at least within the region surrounding the cavity section.

11. A micro chemical device according to any one of claims 1 and 3, wherein at least one of the member (A) and the member (B) is a sheet type member.

12. A micro chemical device according to any one of claims 1, 3 and 4 to 7, wherein the shape of the convex structure is a hemispherical shape.

13. A micro chemical device with a valve function, in which by bonding a member (B) and a member (C) together with a layer type member (D) comprising a lacking section for forming a channel disposed therebetween, a capillary type channel of width from 1 to 1000 μm and height from 1 to 1000 μm is formed between the member (B) and the member (C) by the lacking section of the material of the member (D), and a cavity section is formed partway along the channel and the width of this cavity section is from 0.5 to 100 fold the width of the capillary type channel and the ratio of maximum height/maximum width for the cavity section is not more than 1, and any one of the members (B), (C) and (D) is formed from a soft material with a tensile modulus of elasticity within a range from 0.1 MPa to 700 MPa, at least within the portion which corresponds with the cavity section (or in the case of the member (D), the portion surrounding the cavity section), wherein a member (H) comprising a convex structure is laminated on top of the member (B), with the convex structure facing away from the member (B) and with the positional relationship relative to the member (B) fixed so that the convex structure is in a position corresponding with the cavity section, and is formed from a material with a tensile modulus of elasticity within a range from 10 MPa to 10 GPa, and with a thickness within a range from 0.5 to 500 μm, and any one of the members (B), (C) and (D) is formed from a medium hard material or a hard material with a tensile modulus of elasticity of at least 700 MPa, wherein by compressing the cavity section from the external surface of the member (B), the volume of the cavity section can be reduced in a reversible manner.

14. A micro chemical device according to claim 13, wherein the member (B) is formed from a soft material with a tensile modulus of elasticity within a range from 0.1 MPa to 700 MPa, at least within the portion which corresponds with the cavity section, and the minimum thickness of the portion which corresponds with the cavity section is within a range from 10 to 3000 μm.

15. A micro chemical device according to claim 13, wherein the member (B) is formed from a medium hard material with a tensile modulus of elasticity within a range from 700 MPa to 10 GPa, at least within the portion which corresponds with the cavity section, and the minimum thickness of this portion which corresponds with the cavity section is within a range from 0.5 to 500 μm.

16. A micro chemical device according to any one of claim 13 through claim 15, wherein a sheet type member (E) formed from a medium hard material with a tensile modulus of elasticity within a range from 700 MPa to 10 GPa, and with a thickness within a range from 0.5 to 500 μm, is laminated to the outside of the member (B), at least within the portion which corresponds with the cavity section.

17. A micro chemical device according to any one of claim 13 through claim 14, wherein a convex structure is provided on the surface of the member (B), in a position corresponding with the cavity section.

18. A micro chemical device according to claim 17, wherein the convex structure is formed from a hard material with a tensile modulus of elasticity of at least 700 MPa.

19. A micro chemical device according to claim 17, wherein the shape of the convex structure is a hemispherical shape.

20. A micro chemical device according to any one of claim 13 through claim 15, wherein a member (H) comprising a convex structure is laminated onto the member (B) and the convex structure is fixed in a position corresponding with the cavity section with the convex structure facing the cavity section.

21. A micro chemical device according to claim 20, wherein the member (H) comprises a sheet type member, and the convex structure is attached to the sheet type member.

22. A micro chemical device according to claim 20, wherein the shape of the convex structure is a hemispherical shape.

23. A micro chemical device according to any one of claim 13 through claim 14, wherein the soft material with a tensile modulus of elasticity within a range from 0.1 to 700 MPa is a cured product of a radiation-curable composition.

24. A micro chemical device according to claim 23, wherein the radiation-curable composition comprises an amphipathic radiation-curable compound.

25. A micro chemical device according to any one of claim 13 through claim 15, wherein the medium hard material with a tensile modulus of elasticity within a range from 700 MPa to 10 GPa is a cured product of a radiation-curable composition.

* * * * *